US 7,446,180 B2

(12) United States Patent
Novak

(10) Patent No.: US 7,446,180 B2
(45) Date of Patent: Nov. 4, 2008

(54) CONFORMATIONALLY ABNORMAL FORMS OF TAU PROTEINS AND SPECIFIC ANTIBODIES THERETO

(75) Inventor: Michal Novak, Bratislava (SK)

(73) Assignee: Axon Neuroscience Forschungs-Und Entwicklungs GmbH, Vienna (AU)

( * ) Notice: Subject to any disclaimer, the term of this patent is extended or adjusted under 35 U.S.C. 154(b) by 189 days.

(21) Appl. No.: 10/470,928

(22) PCT Filed: Jan. 29, 2002

(86) PCT No.: PCT/EP02/00897

§ 371 (c)(1),
(2), (4) Date: Nov. 25, 2003

(87) PCT Pub. No.: WO02/062851

PCT Pub. Date: Aug. 15, 2002

(65) Prior Publication Data
US 2004/0082763 A1    Apr. 29, 2004

(30) Foreign Application Priority Data
Feb. 2, 2001   (AT) .............................. A 175/2001

(51) Int. Cl.
*C07K 16/00* (2006.01)
*C12P 21/08* (2006.01)
*A61K 39/395* (2006.01)
*G01N 33/53* (2006.01)

(52) U.S. Cl. .............................. 530/388.1; 530/388.24; 530/387.1; 424/130.1; 424/139.1; 424/141.1; 424/145.1; 435/7.1; 435/7.5; 435/7.7; 435/7.9; 435/7.92

(58) Field of Classification Search .................. None
See application file for complete search history.

(56) References Cited

U.S. PATENT DOCUMENTS 5,733,734 A * 3/1998 Trojanowski et al. ........ 435/7.1

FOREIGN PATENT DOCUMENTS

| WO | WO 94/18560 | 2/1994 |
| WO | WO 02/062851 | 8/2002 |

OTHER PUBLICATIONS

Ksiezak-Reding et al., 1988 (J. Biol. Chemistry,, vol. 263, No. 17, pp. 7943-7947).*
Abraha et al., "C-terminal inhibition of tau assembly in vitro and in Alzheimer's disease," *Journal of Cell Science*, 113:3737-3745, 2000.
Black, "Comparison of the effects of microtubule-associated protein 2 and tau on the packing density of in vitro assembled mirotubles," *Proc. Natl. Acad. Sci., USA*, 84(21):7783-7787, 1987.
Blessed et al., "The association between quantitative measures of demetia and of senile cahnge in the cerebral grey matter of elderly subjects," *Brit. J. Psychiat.*, 114:797-811, 1968.

Blum et al., "Improved silver staining of plant proteins, RNA and DNA in polyacrylamide gels," *Electrophoresis*, 8:93-99, 1987.
Cleveland et al., "Physical and chemical properties of purified tau factor and the role of tau in microtube assembly," *J. Mol. Biol.*, 116:227-247, 1977.
Cleveland et al., "Purification of tau, a microtubule-associated protein that induces assembly of microtubules from purified tubulin," *J. Mol. Biol.*, 116:207-225, 1977.
Cote et al., "Current protocols for light microscopy immunocytochemistry," *Immunohistochemistry II*, A. C. Cuelllo (ed.), John Wiley & Sons., 147-168, 1993.
Crowther et al., "Assembly of Alzheimer-like filaments from full-length tau protein," *FEBS Letters*, 337:135-138, 1994.
Dickson et al., "Cytoskeletal pathology in non-Alzheimer degenerative dementia: new lesions in diffuse Lewy body disease, Pick's disease, and Corticobasal Degenration," *J. Neural Transm.*, (Supp.)47:31-46, 1996.
DiFiglia et al., "Aggregation of Huntingtin in neuronal intranuclear inclusions and dystrophic neurites in brain," *Science*, 277:1990-1993, 1997.
Donofrio et al., "Electroelution for purification of influenza A matrix protein for use in immunoassay," *Journal of Virological Methods*, 13:107-120, 1986.
Drewes et al., "MAP's, MARK's and microtubule dynamics," *TIBS*, 23:307-311, 1998.
Drubin and Kirschner, "Tau protein function in living cells," *The Journal of Cell Biology*, 103:2739-2746, 1986.
Fasulo et al., "Overexpression of Alzheimer's PHF core tau fragments: implications for the tau truncation hypothesis," *Alzheimer's Research*, 2:195-200, 1996.
Forno, "The Lewy body in Parkinson's Disease," *Advances in Neurology*, 45:35-43, 1986.
Goedert et al., "Assembly of microtubule-associated protein tau into Alzheimer-like filaments induced by sulphated glycosaminoglycans," *Nature*, 383, 550-553, 1996.
Goedert et al., "Multiple isoforms of human microtubule-assocaited protein tau: sequences and localization in neurofibrillary tangles of Alzheimer's Disease," *Neuron*, 3:519-526, 1989.
Greenberg and Davies, "A preparation of Alzheimer paired helical filaments that displays distinct τ proteins by polyacrylamide gel electrophoresis," *Proc. Natl. Acad. Sci., USA*, 87:5827-5831, 1990.
Grundke-Iqbal et al., "Abnormal phosphorylation of the microtubule-associated protein $\tau$ (Tau) in Alzheimer cytoskeletal pathology," *Proc. Natl. Acad. Sci., USA*, 83(13):4913-4917, 1986.
Gustke et al., "The Alzheimer-like phosphorylation of tau protein reduces microtubule binding and involves Ser-Pro an dThr-Pro motifs," *FEBS*, 307(2):199-205, 1992.
Himmler, "Structure of the bovine tau gene: alternatively spliced transcripts generate a protein family," *Molecular and Cellular Biology*, 9(4):1389-1396, 1989.

(Continued)

Primary Examiner—Olga N Chernyshev
(74) Attorney, Agent, or Firm—Fulbright & Jaworski LLP

(57) ABSTRACT

Invention relates to antibodies with a specificity to an abnormally truncated form of tau protein which is conformationally different from normal tau and does not bind to normal tau protein, conformationally different tau proteins ("tauons") and diagnostic and therapeutical aspects in relation to Alzheimer's disease and related tauopathies.

14 Claims, 14 Drawing Sheets

OTHER PUBLICATIONS

Hirano and Zimmerman, "Alzheimer's neurofibrillary changes," *Archives of Neurology*, 7:227-242, 1962.

Jicha et al., "Sequnce requirements for formation of conformational variants of tau similar to those found in Alzheiner's disease," *Journal of Neuroscience Research*, 55:713-723, 1999.

Kampers et al., "RNA stimulates aggregation of microtubule-associated protein tau into Alzheimer-like paired helical filaments," *FEBS Letters*, 399:344-349, 1996.

Kenessy et al., "Detection of o-asparate in tau proteins associated with Alzheimer paired helical filaments," *Brain Research*, 675:183-189, 1995.

Kiss et al., "Light microscopic triple-colored immunohistochemical staining on the same vibratome section using the avidin-botin-perioxidase complex technique," *Histochemistry*, 88:353-356, 1988.

Ko et al., "An Immunochemical study on tau glycation in paired helical filaments," *Brain Research*, 830:301-313, 1999.

Kontsekova et al., "Quick purification of recombinant human truncated tau proteins for immunoanalysis," *Journal of Immunological Methods*, 185:245-248, 1995.

Kontsekova et al., "The effect of postfusion cell density on establishment of hybridomas," *Folia Biologica*, 34:19-22, 1988.

Kontsekova, et al., "One-step method for establishing 8-azaguanine-resistant hybridomas suitable for the preparation of triomas," *Journal of Immunological Methods*, 145:247-250, 1991.

Kopke et al., "Microtubule-associated protein tau," *The Journal of Biological Chemistry*, 268(32):24374-24384, 1993.

Kosik et al., "Develpmentally regulated expression of specific tau sequences," *Neuron*, 2:1389-1397, 1989.

Ksiezak-Reding et al., "Assembed tau filaments differ from native paired helical filaments as determined by scanning transmission electrom microscopy (STEM)," *Brain Research*, 814:86-98, 1998.

Laemmli, "Cleavage of structural proteins durin the assembly of the head of bacteriophage T4," *Nature*, 227:680-685, 1970.

Lindwall and Cole, "The purification of tau protein and the occurance of two phosphorylation states of tau in brain," *The Journal of Biological Chemistry*, 259(19):12241-12245, 1984.

LoPresti et al., "Functional implications for the mircotubule-associated protein tau: localization in oligodendrocytes," *Proc. Natl. Acad. Sci., USA*, 92:10369-10373, 1995.

Mori et al., "Ubiquitin is a component of paired helical filaments in Alzheimer's isease," *Science*, 235:1641-16441987.

Nishimura et al., "Immunohistochemical investigation of tau-positive structures in the cerebral cortex of patients with progressive supranuclear palsy," *Neuroscience Letters*, 201:123-126, 1995.

Novak et al., "Difference between the tau protein of Alzheimer paired helical filament core and normal tau revealed by epitope analysis of monoclonal antibodies 423 and 7.51," *Proc. Natl. Acad. Sci., USA*, 88:5837-5841, 1991.

Novak et al., "Molecular characterization of minimal protease resistant tau unit of the Alzheimer's disease paired helical filament," *EMBO Journal*, 12(1):365-370, 1993.

Novak, "Truncated tau protein as a new marker for Alzheimer's disease," *Acta Virology*, 38(3):173-189, 1994.

Paudel and Li, "Heparin-induced conformational change in microtubule-associated protein tau a s detected by chemical cross-linking and phosphopeptide mapping," *The Journal of Biological Chemistry*, 274(12):8029-8038, 1999.

Perez et al., "Polymerization of τ into filaments in the prescence of heparin: the inimal sequence requred for τ-τ interation," *Journal of Neurochemistry*, 67:1183-1190, 1996.

Prusiner, *Human prion diseases and neurodegeneration*, Ed Springer-Verlag, Berlin, 1996.

Reed et al., "The neuropathology of a chromosome 17-linked autosomal dominant parkinsonism and dementia," *Journal of Neuropathology and Experimental Neurology*, 57(6):588-601, 1998.

Roberts, "Immunocytochemistry of neurofibrillary tangles in dementia pugilistica and Alzheimer's disease evidence for common genisis," *The Lancet*, 1456-1458, 1988.

Schneider et al., "Phosphorylation that detaches tau protein from microtubules (Ser262, Ser214) also protects it against aggregation into Alzheimer paired helical filaments," *Biochemistry*, 38:3549-3558, 1999.

Schweers et al., "Oxidation of cysteine-322 in the repeat domain of microtubule-associated protein τ controls the in vitro assembly of paired helical filaments," *Proc. Natl. Acad. Sci., USA*, 92:8463-8467, 1995.

Shankar et al., "Immunocytochemical characterization of neurofibrilary tangles in amyotrophic lateral sclerosis and parkinsonism-dementia of guam," *Ann. Neurol.*, 25:146-151, 1989.

Spillatini et al., "Fronotemporal dementia and Parkinsonism linked t o chromosome 17: A new group of tauopathies," *Brain Pathology*, 8:387-402, 1998.

Scott, "Enhanced chemiluminescence immunoassay," *The Protein Protocols Handbook*, $2^{nd}$ ed., J.M. Walker, Humana Press Inc, Totowa, NJ, 1089-1096, 2002.

Studier and Moffatt, "Use of bacteriophage T7 RNA polymerase to direct selective high-level expression of cloned genes," *J. Mol. Biol.*, 189:113-130, 1986.

Ugolini et al., "Co-localization of truncated tau and DNA fragmentation in Alzheimer's disease neurones," *NeuroReport*, 3709-3712, 1997.

Vallee, "Reversible assembly purification of micotubules without assembly-promoting agents and further purification of tubulin, microtubule-associated proteins, and MAP fragments," *Methods in Enzymology*, 134:89-105, 1986.

Wallis et al., "The mechanism of equilibrium binding of microtubule-associated protein 2 to microtubules," *Journal of Biological Chemistry*, 268:15158-15167, 1993.

Wang et al., "Glycosylation of micotubule-associated protein tau: An abnormal posttranslational modification in Alzheimer's disease," *Nature Medicine*, 2(8):871-875, 1996.

Wilson and Binder, "Free fatty acids stimulate the polymerization of tau and amyloid β peptides," *American Journal of Pathology*, 150(6):2181-2195, 1997.

Wischik et al., "Structural characterization of the core of the paired helical filament of Alzheimer disease," *Proc. Natl. Acad. Sci., USA*, 85(13):4884-4888, 1988.

Wishik et al., "Isolation of a fragment of tau derived from the core of the paired helical filament of Alzheimer disease," *Proc. Natl. Acad. Sci., USA*, 85(12):4506-4510, 1988.

Yan et al., "Glycated tau protein in Alzheimer disease: A mechanism for inductionof oxidant stress," *Proc. Natl. Acad. Sci., USA*, 91:7787-7791, 1994.

Zemlan et al., "Quantification of axonal damage in traumatic brain injury: affinity purification and characterization of cerebrospinal fluid tau proteins," *Journal of Neurochemistry*, 72(2):741-750, 1999.

Matsuo et al., "Biopsy-Derived Adult Human Brain Tau Is Phosphorylated at Many of the Same Sites as Alzheimer's Disease Paired Helical Filament Tau," *Neuron*, 13:989-1002, 1994.

Skrabana et al., "Intrinsically Disordered Proteins in the Neurodegenerative Processes: Formation of Tau Protein Paired Helical Filaments and Their Analysis," *Cellular and Molecular Neurobiology*, 2006.

Japanese Application No. 2002-563203 Official Action, mailed Jan. 15, 2008.

Weaver et al., "Conformational change as one of the earliest alterations of tau in Alzheimer's disease," *Neurobiology of Aging*, 21:719-727, 2000.

* cited by examiner

AD brain

SAMPLE A
↓
homogenize
↓
spin (25 000g) →spt
↓
spin (200 000g) → pellet
↓
extract (8 M urea)
↓
spin (300 000g) → spt
↓
dialyse (TRIS)
↓
precipitate (with dialysis)
↓
spin (200 000g) → spt
↓
dialyse (MES)
↓
PC column
↓
eluate (0 – 1 M NaCl)
↓
dialyse (MES)
↓
speed vac (*fraction I*)

SAMPLE B
↓
homogenize
↓
spin (27 000g) →spt
↓
re-extract pellet
↓
spin (27 000g) →spt
↓
pool spts
↓
adjust to 1% N lauroylsarcosine
        1% • mercapthoethanol
↓
incubate at 37 °C, 3 hr
↓
spin 35 000 rpm → pellet
↓
re-extract pellet
↓
filtrate (0,45um) → spt
↓
spin 35 000 rpm → pellet
↓
extract pellet with 2,5% formic acid
↓
spin (10 000g) → spt (*fraction II*)
↓
pellet (*fraction III*)

Antigen for immunization → pooled fractions I, II, III

FIG. 1

1. Minimal tauon (the numbers indicate the amino acid residues at the respective positions in the longest human tau isoform consisiting of 441 residues).

The N- and C-termini of the minimal tauon can be extended simultaneously, however, without reaching the full lenght of the protein, e.g. 299-401, 298-402, etc.

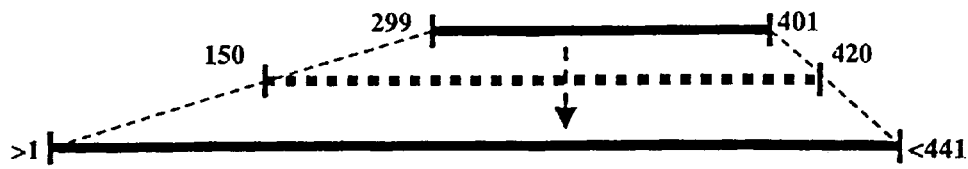

2. C-terminally truncated tauons (the N-terminal residue can vary from amino acid at the position 1 to 299, e.g. 2-400, 3-400, etc.)

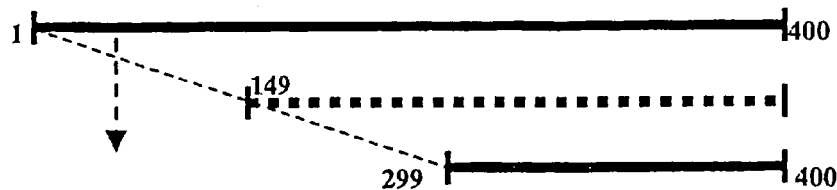

3. N-terminally truncated tauons (the C-terminal residue can be any residue at the positions from 401 to 441, e.g. 300-401, 300-402)

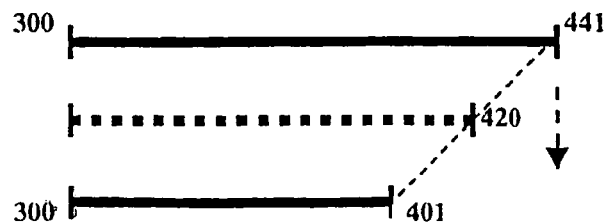

FIG. 2

*SEQ. ID No:1* Minimal tauon

The numbers indicate the amino acid residues at the respective positions in the longest human tau isoform consisting of 441 residues.

```
                                                                    val 300
301 pro gly gly gly ser val gln ile val tyr lys pro val asp leu ser lys val thr ser
321 lys cys gly ser leu gly asn ile his his lys pro gly gly gly gln val glu val lys
341 ser glu lys leu asp phe lys asp arg val gln ser lys ile gly ser leu asp asn ile
361 thr his val pro gly gly gly asn lys lys ile glu thr his lys leu thr phe arg glu
381 asn ala lys ala lys thr asp his gly ala glu ile val tyr lys ser pro val val ser
```

The N- and C-termini of the minimal tauon can be extended simultaneously, however, without reaching the full lenght of the protein, e.g. 299-401, 298-402, etc.

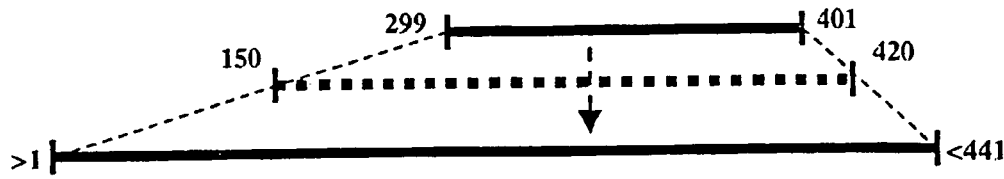

FIG. 3

SEQ. ID No:2    C-terminally truncated tauons 1    met ala glu pro arg gln glu phe glu val met glu asp his ala gly thr tyr gly leu
21   gly asp arg lys asp gln gly gly tyr thr met his gln asp gln glu gly asp thr asp
41   ala gly leu lys glu ser pro leu gln thr pro thr glu asp gly ser glu glu pro gly
61   ser glu thr ser asp ala lys ser thr pro thr ala glu asp val thr ala pro leu val
81   asp glu gly ala pro gly lys gln ala ala ala gln pro his thr glu ile pro glu gly
101  thr thr ala glu glu ala gly ile gly asp thr pro ser leu glu asp glu ala ala gly
121  his val thr gln ala arg met val ser lys ser lys asp gly thr gly ser asp asp lys
141  lys ala lys gly ala asp gly lys thr lys ile ala thr pro arg gly ala ala pro pro
161  gly gln lys gly gln ala asn ala thr arg ile pro ala lys thr pro pro ala pro lys
181  thr pro pro ser ser gly glu pro pro lys ser gly asp arg ser gly tyr ser ser pro
201  gly ser pro gly thr pro gly ser arg ser arg thr pro ser leu pro thr pro pro thr
221  arg glu pro lys lys val ala val val arg thr pro pro lys ser pro ser ser ala lys
241  ser arg leu gln thr ala pro val pro met pro asp leu lys asn val lys ser lys ile
261  gly ser thr glu asn leu lys his gln pro gly gly gly lys val gln ile ile asn lys
281  lys leu asp leu ser asn val gln ser lys cys gly ser lys asp asn ile lys his val
301  pro gly gly gly ser val gln ile val tyr lys pro val asp leu ser lys val thr ser
321  lys cys gly ser leu gly asn ile his his lys pro gly gly gly gln val glu val lys
341  ser glu lys leu asp phe lys asp arg val gln ser lys ile gly ser leu asp asn ile
361  thr his val pro gly gly gly asn lys lys ile glu thr his lys leu thr phe arg glu
381  asn ala lys ala lys thr asp his gly ala glu ile val tyr lys ser pro val val ser The N-terminal residue of the C-terminally truncated tauons can vary from amino acid at the position 1 to position 299, e.g. 2-400, 3-400, etc.

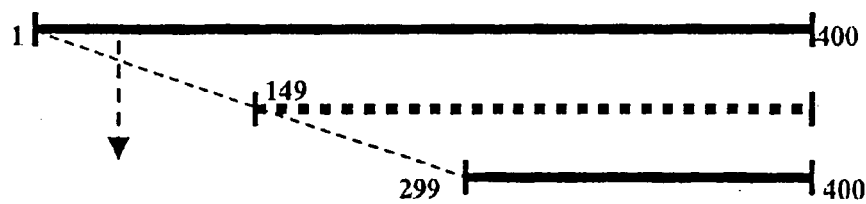

FIG. 4

```
                                                                    val 300
301 pro gly gly gly ser val gln ile val tyr lys pro val asp leu ser lys val thr ser
321 lys cys gly ser leu gly asn ile his his lys pro gly gly gly gln val glu val lys
341 ser glu lys leu asp phe lys asp arg val gln ser lys ile gly ser leu asp asn ile
361 thr his val pro gly gly gly asn lys lys ile glu thr his lys leu thr phe arg glu
381 asn ala lys ala lys thr asp his gly ala glu ile val tyr lys ser pro val val ser
401 gly asp thr ser pro arg his leu ser asn val ser ser thr gly ser ile asp met val
421 asp ser pro gln leu ala thr leu ala asp glu val ser ala ser leu ala lys gln gly
441 leu
```

The C-terminal residue of the N-terminally truncated tauons can be any residue at the positions from 401 to 441, e.g. 300-401, 300-402)

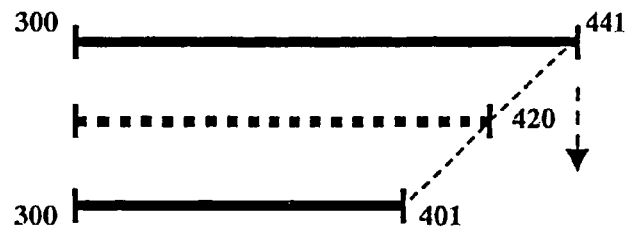

FIG. 5

SEQ ID NO:4

Human tau 37  381aa

```
1
Met ala glu pro arg gln glu phe glu val met glu asp his ala gly thr tyr gly leu
21
gly asp arg lys asp gln gly gly tyr thr met his gln asp gln glu gly asp thr asp
41
ala gly leu lys glu ser pro leu gln thr pro thr glu asp gly ser glu glu pro gly
61
ser glu thr ser asp ala lys ser thr pro thr ala glu ala glu glu ala gly ile gly
81
asp thr pro ser leu glu asp glu ala ala gly his val thr gln ala arg met val ser
101
lys ser lys asp gly thr gly ser asp asp lys lys ala lys gly ala asp gly lys thr
121
lys ile ala thr pro arg gly ala ala pro pro gly gln lys gly gln ala asn ala thr
141
arg ile pro ala lys thr pro pro ala pro lys thr pro pro ser ser gly glu pro pro
161
lys ser gly asp arg ser gly tyr ser ser pro gly ser pro gly thr pro gly ser arg
181
ser arg thr pro ser leu pro thr pro pro thr arg glu pro lys lys val ala val val
201
arg thr pro pro lys ser pro ser ser ala lys ser arg leu gln thr ala pro val pro
221
met pro asp leu lys asn val lys ser lys ile gly ser thr glu asn leu lys his gln
241
pro gly gly gly lys val gln ile val tyr lys pro val asp leu ser lys val thr ser
261
lys cys gly ser leu gly asn ile his his lys pro gly gly gly gln val glu val lys
281
ser glu lys leu asp phe lys asp arg val gln ser lys ile gly ser leu asp asn ile
301
thr his val pro gly gly gly asn lys lys ile glu thr his lys leu thr phe arg glu
321
asn ala lys ala lys thr asp his gly ala glu ile val tyr lys ser pro val val ser
341
gly asp thr ser pro arg his leu ser asn val ser ser thr gly ser ile asp met val
361
asp ser pro gln leu ala thr leu ala asp glu val ser ala ser leu ala lys gln gly
381
leu
```

FIG. 7

SEQ ID NO:5

Human tau 39 | N1 N2 ... R1 R3 R4 R' | 410aa

```
1
Met ala glu pro arg gln glu phe glu val met glu asp his ala gly thr tyr gly leu
21
gly asp arg lys asp gln gly gly tyr thr met his gln asp gln glu gly asp thr asp
41
ala gly leu lys glu ser pro leu gln thr pro thr glu asp gly ser glu glu pro gly
61
ser glu thr ser asp ala lys ser thr pro thr ala glu asp val thr ala pro leu val
81
asp glu gly ala pro gly lys gln ala ala ala gln pro his thr glu ile pro glu gly
101
thr thr ala glu glu ala gly ile gly asp thr pro ser leu glu asp glu ala ala gly
121
his val thr gln ala arg met val ser lys ser lys asp gly thr gly ser asp asp lys
141
lys ala lys gly ala asp gly lys thr lys ile ala thr pro arg gly ala ala pro pro
161
gly gln lys gly gln ala asn ala thr arg ile pro ala lys thr pro pro ala pro lys
181
thr pro pro ser ser gly glu pro pro lys ser gly asp arg ser gly tyr ser ser pro
201
gly ser pro gly thr pro gly ser arg ser arg thr pro ser leu pro thr pro pro thr
221
arg glu pro lys lys val ala val val arg thr pro pro lys ser pro ser ser ala lys
241
ser arg leu gln thr ala pro val pro met pro asp leu lys asn val lys ser lys ile
261
gly ser thr glu asn leu lys his gln pro gly gly gly lys val gln ile val tyr lys
281
pro val asp leu ser lys val thr ser lys cys gly ser leu gly asn ile his his lys
301
pro gly gly gly gln val glu val lys ser glu lys leu asp phe lys asp arg val gln
321
ser lys ile gly ser leu asp asn ile thr his val pro gly gly gly asn lys lys ile
341
glu thr his lys leu thr phe arg glu asn ala lys ala lys thr asp his gly ala glu
361
ile val tyr lys ser pro val val ser gly asp thr ser pro arg his leu ser asn val
381
ser ser thr gly ser ile asp met val asp ser pro gln leu ala thr leu ala asp glu
401
val ser ala ser leu ala lys gln gly leu
```

FIG. 8

SEQ ID NO:6

Human tau 40 [N1 N2 ... R1 R2 R3 R4 R'] 441aa

```
1
Met ala glu pro arg gln glu phe glu val met glu asp his ala gly thr tyr gly leu
21
gly asp arg lys asp gln gly gly tyr thr met his gln asp gln glu gly asp thr asp
41
ala gly leu lys glu ser pro leu gln thr pro thr glu asp gly ser glu glu pro gly
61
ser glu thr ser asp ala lys ser thr pro thr ala glu asp val thr ala pro leu val
81
asp glu gly ala pro gly lys gln ala ala ala gln pro his thr glu ile pro glu gly
101
thr thr ala glu glu ala gly ile gly asp thr pro ser leu glu asp glu ala ala gly
121
his val thr gln ala arg met val ser lys ser lys asp gly thr gly ser asp asp lys
141
lys ala lys gly ala asp gly lys thr lys ile ala thr pro arg gly ala ala pro pro
161
gly gln lys gly gln ala asn ala thr arg ile pro ala lys thr pro pro ala pro lys
181
thr pro pro ser ser gly glu pro pro lys ser gly asp arg ser gly tyr ser ser pro
201
gly ser pro gly thr pro gly ser arg ser arg thr pro ser leu pro thr pro pro thr
221
arg glu pro lys lys val ala val val arg thr pro pro lys ser pro ser ser ala lys
241
ser arg leu gln thr ala pro val pro met pro asp leu lys asn val lys ser lys ile
261
gly ser thr glu asn leu lys his gln pro gly gly gly lys val gln ile ile asn lys
281
lys leu asp leu ser asn val gln ser lys cys gly ser lys asp asn ile lys his val
301
pro gly gly gly ser val gln ile val tyr lys pro val asp leu ser lys val thr ser
321
lys cys gly ser leu gly asn ile his his lys pro gly gly gly gln val glu val lys
341
ser glu lys leu asp phe lys asp arg val gln ser lys ile gly ser leu asp asn ile
361
thr his val pro gly gly gly asn lys lys ile glu thr his lys leu thr phe arg glu
381
asn ala lys ala lys thr asp his gly ala glu ile val tyr lys ser pro val val ser
401
gly asp thr ser pro arg his leu ser asn val ser ser thr gly ser ile asp met val
421
asp ser pro gln leu ala thr leu ala asp glu val ser ala ser leu ala lys gln gly
441
leu
```

FIG. 9

SEQ ID NO:7

Human
tau 43  383aa

```
1
Met ala glu pro arg gln glu phe glu val met glu asp his ala gly thr tyr gly leu
21
gly asp arg lys asp gln gly gly tyr thr met his gln asp gln glu gly asp thr asp
41
ala gly leu lys ala glu glu ala gly ile gly asp thr pro ser leu glu asp glu ala
61
ala gly his val thr gln ala arg met val ser lys ser lys asp gly thr gly ser asp
81
asp lys lys ala lys gly ala asp gly lys thr lys ile ala thr pro arg gly ala ala
101
pro pro gly gln lys gly gln ala asn ala thr arg ile pro ala lys thr pro pro ala
121
pro lys thr pro pro ser ser gly glu pro pro lys ser gly asp arg ser gly tyr ser
141
ser pro gly ser pro gly thr pro gly ser arg ser arg thr pro ser leu pro thr pro
161
pro thr arg glu pro lys lys val ala val val arg thr pro pro lys ser pro ser ser
181
ala lys ser arg leu gln thr ala pro val pro met pro asp leu lys asn val lys ser
201
lys ile gly ser thr glu asn leu lys his gln pro gly gly gly lys val gln ile ile
221
asn lys lys leu asp leu ser asn val gln ser lys cys gly ser lys asp asn ile lys
241
his val pro gly gly gly ser val gln ile val tyr lys pro val asp leu ser lys val
261
thr ser lys cys gly ser leu gly asn ile his his lys pro gly gly gly gln val glu
281
val lys ser glu lys leu asp phe lys asp arg val gln ser lys ile gly ser leu asp
301
asn ile thr his val pro gly gly gly asn lys lys ile glu thr his lys leu thr phe
321
arg glu asn ala lys ala lys thr asp his gly ala glu ile val tyr lys ser pro val
341
val ser gly asp thr ser pro arg his leu ser asn val ser ser thr gly ser ile asp
361
met val asp ser pro gln leu ala thr leu ala asp glu val ser ala ser leu ala lys
381
gln gly leu
```

FIG. 10

SEQ ID NO:8

Human

tau 44 352aa

```
1
Met ala glu pro arg gln glu phe glu val met glu asp his ala gly thr tyr gly leu
21
gly asp arg lys asp gln gly gly tyr thr met his gln asp gln glu gly asp thr asp
41
ala gly leu lys ala glu glu ala gly ile gly asp thr pro ser leu glu asp glu ala
61
ala gly his val thr gln ala arg met val ser lys ser lys asp gly thr gly ser asp
81
asp lys lys ala lys gly ala asp gly lys thr lys ile ala thr pro arg gly ala ala
101
pro pro gly gln lys gly gln ala asn ala thr arg ile pro ala lys thr pro pro ala
121
pro lys thr pro pro ser ser gly glu pro pro lys ser gly asp arg ser gly tyr ser
141
ser pro gly ser pro gly thr pro gly ser arg ser arg thr pro ser leu pro thr pro
161
pro thr arg glu pro lys lys val ala val val arg thr pro pro lys ser pro ser ser
181
ala lys ser arg leu gln thr ala pro val pro met pro asp leu lys asn val lys ser
201
lys ile gly ser thr glu asn leu lys his gln pro gly gly gly lys val gln ile val
221
tyr lys pro val asp leu ser lys val thr ser lys cys gly ser leu gly asn ile his
241
his lys pro gly gly gly gln val glu val lys ser glu lys leu asp phe lys asp arg
261
val gln ser lys ile gly ser leu asp asn ile thr his val pro gly gly gly asn lys
281
lys ile glu thr his lys leu thr phe arg glu asn ala lys ala lys thr asp his gly
301
ala glu ile val tyr lys ser pro val val ser gly asp thr ser pro arg his leu ser
321
asn val ser ser thr gly ser ile asp met val asp ser pro gln leu ala thr leu ala
341
asp glu val ser ala ser leu ala lys gln gly leu
```

FIG. 11

SEQ ID NO:9

Human
tau 46  412aa

```
1
Met ala glu pro arg gln glu phe glu val met glu asp his ala gly thr tyr gly leu
21
gly asp arg lys asp gln gly gly tyr thr met his gln asp gln glu gly asp thr asp
41
ala gly leu lys glu ser pro leu gln thr pro thr glu asp gly ser glu glu pro gly
61
ser glu thr ser asp ala lys ser thr pro thr ala glu ala glu glu ala gly ile gly
81
asp thr pro ser leu glu asp glu ala ala gly his val thr gln ala arg met val ser
101
lys ser lys asp gly thr gly ser asp asp lys lys ala lys gly ala asp gly lys thr
121
lys ile ala thr pro arg gly ala ala pro pro gly gln lys gly gln ala asn ala thr
141
arg ile pro ala lys thr pro pro ala pro lys thr pro pro ser ser gly glu pro pro
161
lys ser gly asp arg ser gly tyr ser ser pro gly ser pro gly thr pro gly ser arg
181
ser arg thr pro ser leu pro thr pro pro thr arg glu pro lys lys val ala val val
201
arg thr pro pro lys ser pro ser ser ala lys ser arg leu gln thr ala pro val pro
221
met pro asp leu lys asn val lys ser lys ile gly ser thr glu asn leu lys his gln
241
pro gly gly gly lys val gln ile ile asn lys lys leu asp leu ser asn val gln ser
261
lys cys gly ser lys asp asn ile lys his val pro gly gly gly ser val gln ile val
281
tyr lys pro val asp leu ser lys val thr ser lys cys gly ser leu gly asn ile his
301
his lys pro gly gly gly gln val glu val lys ser glu lys leu asp phe lys asp arg
321
val gln ser lys ile gly ser leu asp asn ile thr his val pro gly gly gly asn lys
341
lys ile glu thr his lys leu thr phe arg glu asn ala lys ala lys thr asp his gly
361
ala glu ile val tyr lys ser pro val val ser gly asp thr ser pro arg his leu ser
381
asn val ser ser thr gly ser ile asp met val asp ser pro gln leu ala thr leu ala
401
asp glu val ser ala ser leu ala lys gln gly leu
```

FIG. 12

SEQ ID NO:10

Rat big tau  686aa

```
1
Met ala glu pro arg gln glu phe asp thr met glu asp gln ala gly asp tyr thr met
21
leu gln asp gln glu gly asp met asp his gly leu lys glu ser pro pro gln pro pro
41
ala asp asp gly ser glu glu pro gly ser glu thr ser asp ala lys ser thr pro thr
61
ala glu asp val thr ala pro leu val glu glu arg ala pro asp lys gln ala thr ala
81
gln ser his thr glu ile pro glu gly thr thr ala glu glu ala gly ile gly asp thr
101
pro asn met glu asp gln ala ala gly his val thr gln glu pro gln lys val glu ile
121
phe ser gln ser leu leu val glu pro gly arg arg glu gly gln ala pro asp ser gly
141
ile ser asp trp thr his gln gln val pro ser met ser gly ala pro leu pro pro gln
161
gly leu arg glu ala thr his gln pro leu gly thr arg pro glu asp val glu arg ser
181
his pro ala ser glu leu leu trp gln glu ser pro gln lys glu ala trp gly lys asp
201
arg leu gly ser glu glu glu val asp glu asp ile thr met asp glu ser ser gln glu
221
ser pro pro ser gln ala ser leu ala pro gly thr ala thr pro gln ala arg ser val
241
ser ala ser gly val ser gly glu thr thr ser ile pro gly phe pro ala glu gly ser
261
ile pro leu pro ala asp phe phe ser lys val ser ala glu thr gln ala ser pro pro
281
glu gly pro gly thr gly pro ser glu glu gly his glu ala ala pro glu phe thr phe
301
his val glu ile lys ala ser ala pro lys glu gln asp leu glu gly ala thr val val
321
gly ala pro ala glu glu gln lys ala arg gly pro ser val gly lys gly thr lys glu
341
ala ser leu leu glu pro thr asp lys gln pro ala ala gly leu pro gly arg pro val
361
ser arg val pro gln leu lys ala arg val ala gly val ser lys asp arg thr gly asn
381
asp glu lys lys ala lys gly ala asp gly lys thr gly ala lys ile ala thr pro arg
401
gly ala ala thr pro gly gln lys gly thr ser asn ala thr arg ile pro ala lys thr
421
thr pro ser pro lys thr pro pro gly ser gly glu pro pro lys ser gly glu arg ser
441
gly tyr ser ser pro gly ser pro gly thr pro gly ser arg ser arg thr pro ser leu
461
pro thr pro pro thr arg glu pro lys lys val ala val val arg thr pro pro lys ser
481
pro ser ala ser lys ser arg leu gln thr ala pro val pro met pro asp leu lys asn
501
val arg ser lys ile gly ser thr glu asn leu lys his gln pro gly gly gly lys val
521
```

FIG. 13A

```
gln ile ile asn lys lys leu asp leu ser asn val gln ser lys cys gly ser lys asp
541
asn ile lys his val pro gly gly gly ser val his ile val tyr lys pro val asp leu
561
ser lys val thr ser lys cys gly ser leu gly asn ile his his lys pro gly gly gly
581
gln val glu val lys ser glu lys leu asp phe lys asp arg val gln ser lys ile gly
601
ser leu asp asn ile thr his val pro gly gly gly asn lys lys ile glu thr his lys
621
leu thr phe arg glu asn ala lys ala lys thr asp his gly ala glu ile val tyr lys
641
ser pro val val ser gly asp thr ser pro arg his leu ser asn val ser ser thr gly
661
ser ile asp met val asp ser pro gln leu ala thr leu ala asp glu val ser ala ser
681
leu ala lys gln gly leu
```

FIG. 13B

SEQUENCE LISTING

```
<160> NUMBER OF SEQ ID NOS: 10

<210> SEQ ID NO 1
<211> LENGTH: 101
<212> TYPE: PRT
<213> ORGANISM: Homo sapiens

<400> SEQUENCE: 1

Val Pro Gly Gly Gly Ser Val Gln Ile Val Tyr Lys Pro Val Asp Leu
1               5                   10                  15

Ser Lys Val Thr Ser Lys Cys Gly Ser Leu Gly Asn Ile His His Lys
                20                  25                  30

Pro Gly Gly Gly Gln Val Glu Val Lys Ser Glu Lys Leu Asp Phe Lys
            35                  40                  45

Asp Arg Val Gln Ser Lys Ile Gly Ser Leu Asp Asn Ile Thr His Val
        50                  55                  60

Pro Gly Gly Gly Asn Lys Lys Ile Glu Thr His Lys Leu Thr Phe Arg
65                  70                  75                  80

Glu Asn Ala Lys Ala Lys Thr Asp His Gly Ala Glu Ile Val Tyr Lys
                85                  90                  95
```

Ser Pro Val Val Ser
            100

<210> SEQ ID NO 2
<211> LENGTH: 400
<212> TYPE: PRT
<213> ORGANISM: Homo sapiens

<400> SEQUENCE: 2

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Glu Ser Pro Leu
        35                  40                  45

Gln Thr Pro Thr Glu Asp Gly Ser Glu Glu Pro Gly Ser Glu Thr Ser
    50                  55                  60

Asp Ala Lys Ser Thr Pro Thr Ala Glu Asp Val Thr Ala Pro Leu Val
65                  70                  75                  80

Asp Glu Gly Ala Pro Gly Lys Gln Ala Ala Ala Gln Pro His Thr Glu
                85                  90                  95

Ile Pro Glu Gly Thr Thr Ala Glu Glu Ala Gly Ile Gly Asp Thr Pro
            100                 105                 110

Ser Leu Glu Asp Glu Ala Ala Gly His Val Thr Gln Ala Arg Met Val
        115                 120                 125

Ser Lys Ser Lys Asp Gly Thr Gly Ser Asp Asp Lys Lys Ala Lys Gly
    130                 135                 140

Ala Asp Gly Lys Thr Lys Ile Ala Thr Pro Arg Gly Ala Ala Pro Pro
145                 150                 155                 160

Gly Gln Lys Gly Gln Ala Asn Ala Thr Arg Ile Pro Ala Lys Thr Pro
                165                 170                 175

Pro Ala Pro Lys Thr Pro Pro Ser Ser Gly Glu Pro Pro Lys Ser Gly
            180                 185                 190

Asp Arg Ser Gly Tyr Ser Ser Pro Gly Ser Pro Gly Thr Pro Gly Ser
        195                 200                 205

Arg Ser Arg Thr Pro Ser Leu Pro Thr Pro Pro Thr Arg Glu Pro Lys
    210                 215                 220

Lys Val Ala Val Val Arg Thr Pro Pro Lys Ser Pro Ser Ser Ala Lys
225                 230                 235                 240

Ser Arg Leu Gln Thr Ala Pro Val Pro Met Pro Asp Leu Lys Asn Val
                245                 250                 255

Lys Ser Lys Ile Gly Ser Thr Glu Asn Leu Lys His Gln Pro Gly Gly
            260                 265                 270

Gly Lys Val Gln Ile Ile Asn Lys Lys Leu Asp Leu Ser Asn Val Gln
        275                 280                 285

Ser Lys Cys Gly Ser Lys Asp Asn Ile Lys His Val Pro Gly Gly Gly
    290                 295                 300

Ser Val Gln Ile Val Tyr Lys Pro Val Asp Leu Ser Lys Val Thr Ser
305                 310                 315                 320

Lys Cys Gly Ser Leu Gly Asn Ile His His Lys Pro Gly Gly Gly Gln
                325                 330                 335

Val Glu Val Lys Ser Glu Lys Leu Asp Phe Lys Asp Arg Val Gln Ser
            340                 345                 350

Lys Ile Gly Ser Leu Asp Asn Ile Thr His Val Pro Gly Gly Gly Asn

-continued

```
                355                 360                 365
Lys Lys Ile Glu Thr His Lys Leu Thr Phe Arg Glu Asn Ala Lys Ala
    370                 375                 380
Lys Thr Asp His Gly Ala Glu Ile Val Tyr Lys Ser Pro Val Val Ser
385                 390                 395                 400

<210> SEQ ID NO 3
<211> LENGTH: 142
<212> TYPE: PRT
<213> ORGANISM: Homo sapiens

<400> SEQUENCE: 3

Val Pro Gly Gly Gly Ser Val Gln Ile Val Tyr Lys Pro Val Asp Leu
1               5                   10                  15

Ser Lys Val Thr Ser Lys Cys Gly Ser Leu Gly Asn Ile His His Lys
            20                  25                  30

Pro Gly Gly Gly Gln Val Glu Val Lys Ser Glu Lys Leu Asp Phe Lys
        35                  40                  45

Asp Arg Val Gln Ser Lys Ile Gly Ser Leu Asp Asn Ile Thr His Val
    50                  55                  60

Pro Gly Gly Gly Asn Lys Lys Ile Glu Thr His Lys Leu Thr Phe Arg
65                  70                  75                  80

Glu Asn Ala Lys Ala Lys Thr Asp His Gly Ala Glu Ile Val Tyr Lys
                85                  90                  95

Ser Pro Val Val Ser Gly Asp Thr Ser Pro Arg His Leu Ser Asn Val
            100                 105                 110

Ser Ser Thr Gly Ser Ile Asp Met Val Asp Ser Pro Gln Leu Ala Thr
        115                 120                 125

Leu Ala Asp Glu Val Ser Ala Ser Leu Ala Lys Gln Gly Leu
    130                 135                 140

<210> SEQ ID NO 4
<211> LENGTH: 381
<212> TYPE: PRT
<213> ORGANISM: Homo sapiens

<400> SEQUENCE: 4

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Glu Ser Pro Leu
        35                  40                  45

Gln Thr Pro Thr Glu Asp Gly Ser Glu Glu Pro Gly Ser Glu Thr Ser
    50                  55                  60

Asp Ala Lys Ser Thr Pro Thr Ala Glu Ala Glu Glu Ala Gly Ile Gly
65                  70                  75                  80

Asp Thr Pro Ser Leu Glu Asp Glu Ala Ala Gly His Val Thr Gln Ala
                85                  90                  95

Arg Met Val Ser Lys Ser Lys Asp Gly Thr Gly Ser Asp Asp Lys Lys
            100                 105                 110

Ala Lys Gly Ala Asp Gly Lys Thr Lys Ile Ala Thr Pro Arg Gly Ala
        115                 120                 125

Ala Pro Pro Gly Gln Lys Gly Gln Ala Asn Ala Thr Arg Ile Pro Ala
    130                 135                 140

Lys Thr Pro Pro Ala Pro Lys Thr Pro Pro Ser Ser Gly Glu Pro Pro
```

```
                145                 150                 155                 160
Lys Ser Gly Asp Arg Ser Gly Tyr Ser Ser Pro Gly Ser Pro Gly Thr
                    165                 170                 175
Pro Gly Ser Arg Ser Arg Thr Pro Ser Leu Pro Thr Pro Pro Thr Arg
                    180                 185                 190
Glu Pro Lys Lys Val Ala Val Val Arg Thr Pro Pro Lys Ser Pro Ser
                    195                 200                 205
Ser Ala Lys Ser Arg Leu Gln Thr Ala Pro Val Pro Met Pro Asp Leu
    210                 215                 220
Lys Asn Val Lys Ser Lys Ile Gly Ser Thr Glu Asn Leu Lys His Gln
225                 230                 235                 240
Pro Gly Gly Gly Lys Val Gln Ile Val Tyr Lys Pro Val Asp Leu Ser
                245                 250                 255
Lys Val Thr Ser Lys Cys Gly Ser Leu Gly Asn Ile His His Lys Pro
                260                 265                 270
Gly Gly Gly Gln Val Glu Val Lys Ser Glu Lys Leu Asp Phe Lys Asp
                275                 280                 285
Arg Val Gln Ser Lys Ile Gly Ser Leu Asp Asn Ile Thr His Val Pro
            290                 295                 300
Gly Gly Gly Asn Lys Lys Ile Glu Thr His Lys Leu Thr Phe Arg Glu
305                 310                 315                 320
Asn Ala Lys Ala Lys Thr Asp His Gly Ala Glu Ile Val Tyr Lys Ser
                325                 330                 335
Pro Val Val Ser Gly Asp Thr Ser Pro Arg His Leu Ser Asn Val Ser
                340                 345                 350
Ser Thr Gly Ser Ile Asp Met Val Asp Ser Pro Gln Leu Ala Thr Leu
                355                 360                 365
Ala Asp Glu Val Ser Ala Ser Leu Ala Lys Gln Gly Leu
            370                 375                 380

<210> SEQ ID NO 5
<211> LENGTH: 410
<212> TYPE: PRT
<213> ORGANISM: Homo sapiens

<400> SEQUENCE: 5

Met Ala Glu Pro Arg Gln Glu Phe Glu Val Met Glu Asp His Ala Gly
1               5                   10                  15
Thr Tyr Gly Leu Gly Asp Arg Lys Asp Gln Gly Gly Tyr Thr Met His
                20                  25                  30
Gln Asp Gln Glu Gly Asp Thr Asp Ala Gly Leu Lys Glu Ser Pro Leu
            35                  40                  45
Gln Thr Pro Thr Glu Asp Gly Ser Glu Glu Pro Gly Ser Glu Thr Ser
        50                  55                  60
Asp Ala Lys Ser Thr Pro Thr Ala Glu Asp Val Thr Ala Pro Leu Val
65                  70                  75                  80
Asp Glu Gly Ala Pro Gly Lys Gln Ala Ala Ala Gln Pro His Thr Glu
                85                  90                  95
Ile Pro Glu Gly Thr Thr Ala Glu Glu Ala Gly Ile Gly Asp Thr Pro
                100                 105                 110
Ser Leu Glu Asp Glu Ala Ala Gly His Val Thr Gln Ala Arg Met Val
            115                 120                 125
Ser Lys Ser Lys Asp Gly Thr Gly Ser Asp Asp Lys Lys Ala Lys Gly
        130                 135                 140
```

```
Ala Asp Gly Lys Thr Lys Ile Ala Thr Pro Arg Gly Ala Pro Pro
145                 150                 155                 160

Gly Gln Lys Gly Gln Ala Asn Ala Thr Arg Ile Pro Ala Lys Thr Pro
            165                 170                 175

Pro Ala Pro Lys Thr Pro Pro Ser Ser Gly Glu Pro Pro Lys Ser Gly
            180                 185                 190

Asp Arg Ser Gly Tyr Ser Ser Pro Gly Ser Pro Gly Thr Pro Gly Ser
            195                 200                 205

Arg Ser Arg Thr Pro Ser Leu Pro Thr Pro Thr Arg Glu Pro Lys
210                 215                 220

Lys Val Ala Val Val Arg Thr Pro Pro Lys Ser Pro Ser Ser Ala Lys
225                 230                 235                 240

Ser Arg Leu Gln Thr Ala Pro Val Pro Met Pro Asp Leu Lys Asn Val
            245                 250                 255

Lys Ser Lys Ile Gly Ser Thr Glu Asn Leu Lys His Gln Pro Gly Gly
            260                 265                 270

Gly Lys Val Gln Ile Val Tyr Lys Pro Val Asp Leu Ser Lys Val Thr
            275                 280                 285

Ser Lys Cys Gly Ser Leu Gly Asn Ile His His Lys Pro Gly Gly Gly
290                 295                 300

Gln Val Glu Val Lys Ser Glu Lys Leu Asp Phe Lys Asp Arg Val Gln
305                 310                 315                 320

Ser Lys Ile Gly Ser Leu Asp Asn Ile Thr His Val Pro Gly Gly Gly
            325                 330                 335

Asn Lys Lys Ile Glu Thr His Lys Leu Thr Phe Arg Glu Asn Ala Lys
            340                 345                 350

Ala Lys Thr Asp His Gly Ala Glu Ile Val Tyr Lys Ser Pro Val Val
            355                 360                 365

Ser Gly Asp Thr Ser Pro Arg His Leu Ser Asn Val Ser Ser Thr Gly
            370                 375                 380

Ser Ile Asp Met Val Asp Ser Pro Gln Leu Ala Thr Leu Ala Asp Glu
385                 390                 395                 400

Val Ser Ala Ser Leu Ala Lys Gln Gly Leu
                405                 410

<210> SEQ ID NO 6
<211> LENGTH: 441
<212> TYPE: PRT
<213> ORGANISM: Homo sapiens

<400> SEQUENCE: 6

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
                20                  25                  30

Gln Asp Gln Glu Gly Asp Thr Asp Ala Gly Leu Lys Glu Ser Pro Leu
            35                  40                  45

Gln Thr Pro Thr Glu Asp Gly Ser Glu Glu Pro Gly Ser Glu Thr Ser
    50                  55                  60

Asp Ala Lys Ser Thr Pro Thr Ala Glu Asp Val Thr Ala Pro Leu Val
65                  70                  75                  80

Asp Glu Gly Ala Pro Gly Lys Gln Ala Ala Gln Pro His Thr Glu
                85                  90                  95

Ile Pro Glu Gly Thr Thr Ala Glu Ala Gly Ile Gly Asp Thr Pro
            100                 105                 110
```

Ser Leu Glu Asp Glu Ala Ala Gly His Val Thr Gln Ala Arg Met Val
            115                 120                 125

Ser Lys Ser Lys Asp Gly Thr Gly Ser Asp Asp Lys Lys Ala Lys Gly
        130                 135                 140

Ala Asp Gly Lys Thr Lys Ile Ala Thr Pro Arg Gly Ala Ala Pro Pro
145                 150                 155                 160

Gly Gln Lys Gly Gln Ala Asn Ala Thr Arg Ile Pro Ala Lys Thr Pro
                165                 170                 175

Pro Ala Pro Lys Thr Pro Pro Ser Ser Gly Glu Pro Pro Lys Ser Gly
            180                 185                 190

Asp Arg Ser Gly Tyr Ser Ser Pro Gly Ser Pro Gly Thr Pro Gly Ser
        195                 200                 205

Arg Ser Arg Thr Pro Ser Leu Pro Thr Pro Pro Thr Arg Glu Pro Lys
    210                 215                 220

Lys Val Ala Val Val Arg Thr Pro Pro Lys Ser Pro Ser Ser Ala Lys
225                 230                 235                 240

Ser Arg Leu Gln Thr Ala Pro Val Pro Met Pro Asp Leu Lys Asn Val
                245                 250                 255

Lys Ser Lys Ile Gly Ser Thr Glu Asn Leu Lys His Gln Pro Gly Gly
            260                 265                 270

Gly Lys Val Gln Ile Ile Asn Lys Lys Leu Asp Leu Ser Asn Val Gln
        275                 280                 285

Ser Lys Cys Gly Ser Lys Asp Asn Ile Lys His Val Pro Gly Gly Gly
    290                 295                 300

Ser Val Gln Ile Val Tyr Lys Pro Val Asp Leu Ser Lys Val Thr Ser
305                 310                 315                 320

Lys Cys Gly Ser Leu Gly Asn Ile His His Lys Pro Gly Gly Gly Gln
                325                 330                 335

Val Glu Val Lys Ser Glu Lys Leu Asp Phe Lys Asp Arg Val Gln Ser
            340                 345                 350

Lys Ile Gly Ser Leu Asp Asn Ile Thr His Val Pro Gly Gly Gly Asn
        355                 360                 365

Lys Lys Ile Glu Thr His Lys Leu Thr Phe Arg Glu Asn Ala Lys Ala
    370                 375                 380

Lys Thr Asp His Gly Ala Glu Ile Val Tyr Lys Ser Pro Val Val Ser
385                 390                 395                 400

Gly Asp Thr Ser Pro Arg His Leu Ser Asn Val Ser Ser Thr Gly Ser
                405                 410                 415

Ile Asp Met Val Asp Ser Pro Gln Leu Ala Thr Leu Ala Asp Glu Val
            420                 425                 430

Ser Ala Ser Leu Ala Lys Gln Gly Leu
        435                 440

<210> SEQ ID NO 7
<211> LENGTH: 383
<212> TYPE: PRT
<213> ORGANISM: Homo sapiens

<400> SEQUENCE: 7

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Ala Glu Glu Ala

```
            35                  40                  45
Gly Ile Gly Asp Thr Pro Ser Leu Glu Asp Glu Ala Ala Gly His Val
 50                  55                  60

Thr Gln Ala Arg Met Val Ser Lys Ser Lys Asp Gly Thr Gly Ser Asp
 65                  70                  75                  80

Asp Lys Lys Ala Lys Gly Ala Asp Gly Lys Thr Lys Ile Ala Thr Pro
                 85                  90                  95

Arg Gly Ala Ala Pro Pro Gly Gln Lys Gly Gln Ala Asn Ala Thr Arg
            100                 105                 110

Ile Pro Ala Lys Thr Pro Pro Ala Pro Lys Thr Pro Pro Ser Ser Gly
        115                 120                 125

Glu Pro Pro Lys Ser Gly Asp Arg Ser Gly Tyr Ser Ser Pro Gly Ser
    130                 135                 140

Pro Gly Thr Pro Gly Ser Arg Ser Arg Thr Pro Ser Leu Pro Thr Pro
145                 150                 155                 160

Pro Thr Arg Glu Pro Lys Lys Val Ala Val Arg Thr Pro Pro Lys
                165                 170                 175

Ser Pro Ser Ser Ala Lys Ser Arg Leu Gln Thr Ala Pro Val Pro Met
            180                 185                 190

Pro Asp Leu Lys Asn Val Lys Ser Lys Ile Gly Ser Thr Glu Asn Leu
        195                 200                 205

Lys His Gln Pro Gly Gly Gly Lys Val Gln Ile Ile Asn Lys Lys Leu
    210                 215                 220

Asp Leu Ser Asn Val Gln Ser Lys Cys Gly Ser Lys Asp Asn Ile Lys
225                 230                 235                 240

His Val Pro Gly Gly Gly Ser Val Gln Ile Val Tyr Lys Pro Val Asp
                245                 250                 255

Leu Ser Lys Val Thr Ser Lys Cys Gly Ser Leu Gly Asn Ile His His
            260                 265                 270

Lys Pro Gly Gly Gly Gln Val Glu Val Lys Ser Glu Lys Leu Asp Phe
        275                 280                 285

Lys Asp Arg Val Gln Ser Lys Ile Gly Ser Leu Asp Asn Ile Thr His
    290                 295                 300

Val Pro Gly Gly Gly Asn Lys Lys Ile Glu Thr His Lys Leu Thr Phe
305                 310                 315                 320

Arg Glu Asn Ala Lys Ala Lys Thr Asp His Gly Ala Glu Ile Val Tyr
                325                 330                 335

Lys Ser Pro Val Val Ser Gly Asp Thr Ser Pro Arg His Leu Ser Asn
            340                 345                 350

Val Ser Ser Thr Gly Ser Ile Asp Met Val Asp Ser Pro Gln Leu Ala
        355                 360                 365

Thr Leu Ala Asp Glu Val Ser Ala Ser Leu Ala Lys Gln Gly Leu
    370                 375                 380

<210> SEQ ID NO 8
<211> LENGTH: 352
<212> TYPE: PRT
<213> ORGANISM: Homo sapiens

<400> SEQUENCE: 8

Met Ala Glu Pro Arg Gln Glu Phe Glu Val Met Glu Asp His Ala Gly
  1               5                  10                  15

Thr Tyr Gly Leu Gly Asp Arg Lys Asp Gln Gly Gly Tyr Thr Met His
             20                  25                  30
```

```
Gln Asp Gln Glu Gly Asp Thr Asp Ala Gly Leu Lys Ala Glu Glu Ala
            35                  40                  45

Gly Ile Gly Asp Thr Pro Ser Leu Glu Asp Glu Ala Ala Gly His Val
        50                  55                  60

Thr Gln Ala Arg Met Val Ser Lys Ser Lys Asp Gly Thr Gly Ser Asp
 65                  70                  75                  80

Asp Lys Lys Ala Lys Gly Ala Asp Gly Lys Thr Lys Ile Ala Thr Pro
                85                  90                  95

Arg Gly Ala Ala Pro Pro Gly Gln Lys Gly Gln Ala Asn Ala Thr Arg
            100                 105                 110

Ile Pro Ala Lys Thr Pro Pro Ala Pro Lys Thr Pro Pro Ser Ser Gly
            115                 120                 125

Glu Pro Pro Lys Ser Gly Asp Arg Ser Gly Tyr Ser Ser Pro Gly Ser
            130                 135                 140

Pro Gly Thr Pro Gly Ser Arg Ser Arg Thr Pro Ser Leu Pro Thr Pro
145                 150                 155                 160

Pro Thr Arg Glu Pro Lys Lys Val Ala Val Val Arg Thr Pro Pro Lys
                165                 170                 175

Ser Pro Ser Ser Ala Lys Ser Arg Leu Gln Thr Ala Pro Val Pro Met
            180                 185                 190

Pro Asp Leu Lys Asn Val Lys Ser Lys Ile Gly Ser Thr Glu Asn Leu
            195                 200                 205

Lys His Gln Pro Gly Gly Gly Lys Val Gln Ile Val Tyr Lys Pro Val
            210                 215                 220

Asp Leu Ser Lys Val Thr Ser Lys Cys Gly Ser Leu Gly Asn Ile His
225                 230                 235                 240

His Lys Pro Gly Gly Gly Gln Val Glu Val Lys Ser Glu Lys Leu Asp
                245                 250                 255

Phe Lys Asp Arg Val Gln Ser Lys Ile Gly Ser Leu Asp Asn Ile Thr
            260                 265                 270

His Val Pro Gly Gly Gly Asn Lys Lys Ile Glu Thr His Lys Leu Thr
            275                 280                 285

Phe Arg Glu Asn Ala Lys Ala Lys Thr Asp His Gly Ala Glu Ile Val
            290                 295                 300

Tyr Lys Ser Pro Val Val Ser Gly Asp Thr Ser Pro Arg His Leu Ser
305                 310                 315                 320

Asn Val Ser Ser Thr Gly Ser Ile Asp Met Val Asp Ser Pro Gln Leu
                325                 330                 335

Ala Thr Leu Ala Asp Glu Val Ser Ala Ser Leu Ala Lys Gln Gly Leu
            340                 345                 350

<210> SEQ ID NO 9
<211> LENGTH: 412
<212> TYPE: PRT
<213> ORGANISM: Homo sapiens

<400> SEQUENCE: 9

Met Ala Glu Pro Arg Gln Glu Phe Glu Val Met Glu Asp His Ala Gly
 1               5                  10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Glu Ser Pro Leu
            35                  40                  45

Gln Thr Pro Thr Glu Asp Gly Ser Glu Glu Pro Gly Ser Glu Thr Ser
        50                  55                  60
```

```
Asp Ala Lys Ser Thr Pro Thr Ala Glu Ala Glu Ala Gly Ile Gly
 65                  70                  75                  80

Asp Thr Pro Ser Leu Glu Asp Glu Ala Ala Gly His Val Thr Gln Ala
                 85                  90                  95

Arg Met Val Ser Lys Ser Lys Asp Gly Thr Gly Ser Asp Asp Lys Lys
                100                 105                 110

Ala Lys Gly Ala Asp Gly Lys Thr Lys Ile Ala Thr Pro Arg Gly Ala
            115                 120                 125

Ala Pro Pro Gly Gln Lys Gly Gln Ala Asn Ala Thr Arg Ile Pro Ala
            130                 135                 140

Lys Thr Pro Pro Ala Pro Lys Thr Pro Ser Ser Gly Glu Pro Pro
145                 150                 155                 160

Lys Ser Gly Asp Arg Ser Gly Tyr Ser Ser Pro Gly Ser Pro Gly Thr
                165                 170                 175

Pro Gly Ser Arg Ser Arg Thr Pro Ser Leu Pro Thr Pro Pro Thr Arg
                180                 185                 190

Glu Pro Lys Lys Val Ala Val Val Arg Thr Pro Pro Lys Ser Pro Ser
                195                 200                 205

Ser Ala Lys Ser Arg Leu Gln Thr Ala Pro Val Pro Met Pro Asp Leu
                210                 215                 220

Lys Asn Val Lys Ser Lys Ile Gly Ser Thr Glu Asn Leu Lys His Gln
225                 230                 235                 240

Pro Gly Gly Gly Lys Val Gln Ile Ile Asn Lys Lys Leu Asp Leu Ser
                245                 250                 255

Asn Val Gln Ser Lys Cys Gly Ser Lys Asp Asn Ile Lys His Val Pro
                260                 265                 270

Gly Gly Gly Ser Val Gln Ile Val Tyr Lys Pro Val Asp Leu Ser Lys
                275                 280                 285

Val Thr Ser Lys Cys Gly Ser Leu Gly Asn Ile His His Lys Pro Gly
                290                 295                 300

Gly Gly Gln Val Glu Val Lys Ser Glu Lys Leu Asp Phe Lys Asp Arg
305                 310                 315                 320

Val Gln Ser Lys Ile Gly Ser Leu Asp Asn Ile Thr His Val Pro Gly
                325                 330                 335

Gly Gly Asn Lys Lys Ile Glu Thr His Lys Leu Thr Phe Arg Glu Asn
                340                 345                 350

Ala Lys Ala Lys Thr Asp His Gly Ala Glu Ile Val Tyr Lys Ser Pro
                355                 360                 365

Val Val Ser Gly Asp Thr Ser Pro Arg His Leu Ser Asn Val Ser Ser
                370                 375                 380

Thr Gly Ser Ile Asp Met Val Asp Ser Pro Gln Leu Ala Thr Leu Ala
385                 390                 395                 400

Asp Glu Val Ser Ala Ser Leu Ala Lys Gln Gly Leu
                405                 410

<210> SEQ ID NO 10
<211> LENGTH: 686
<212> TYPE: PRT
<213> ORGANISM: rat

<400> SEQUENCE: 10

Met Ala Glu Pro Arg Gln Glu Phe Asp Thr Met Glu Asp Gln Ala Gly
1               5                   10                  15

Asp Tyr Thr Met Leu Gln Asp Gln Glu Gly Asp Met Asp His Gly Leu
```

```
                    20                  25                  30
Lys Glu Ser Pro Pro Gln Pro Ala Asp Asp Gly Ser Glu Pro
            35                  40                  45

Gly Ser Glu Thr Ser Asp Ala Lys Ser Thr Pro Thr Ala Glu Asp Val
50                  55                  60

Thr Ala Pro Leu Val Glu Glu Arg Ala Pro Asp Lys Gln Ala Thr Ala
65                  70                  75                  80

Gln Ser His Thr Glu Ile Pro Glu Gly Thr Ala Glu Glu Ala Gly
            85                  90                  95

Ile Gly Asp Thr Pro Asn Met Glu Asp Gln Ala Ala Gly His Val Thr
            100                 105                 110

Gln Glu Pro Gln Lys Val Glu Ile Phe Ser Gln Ser Leu Leu Val Glu
            115                 120                 125

Pro Gly Arg Arg Glu Gly Gln Ala Pro Asp Ser Gly Ile Ser Asp Trp
            130                 135                 140

Thr His Gln Gln Val Pro Ser Met Ser Gly Ala Pro Leu Pro Pro Gln
145                 150                 155                 160

Gly Leu Arg Glu Ala Thr His Gln Pro Leu Gly Thr Arg Pro Glu Asp
            165                 170                 175

Val Glu Arg Ser His Pro Ala Ser Glu Leu Leu Trp Gln Glu Ser Pro
            180                 185                 190

Gln Lys Glu Ala Trp Gly Lys Asp Arg Leu Gly Ser Glu Glu Val
            195                 200                 205

Asp Glu Asp Ile Thr Met Asp Glu Ser Ser Gln Glu Ser Pro Pro Ser
            210                 215                 220

Gln Ala Ser Leu Ala Pro Gly Thr Ala Thr Pro Gln Ala Arg Ser Val
225                 230                 235                 240

Ser Ala Ser Gly Val Ser Gly Glu Thr Thr Ser Ile Pro Gly Phe Pro
            245                 250                 255

Ala Glu Gly Ser Ile Pro Leu Pro Ala Asp Phe Phe Ser Lys Val Ser
            260                 265                 270

Ala Glu Thr Gln Ala Ser Pro Pro Glu Gly Pro Gly Thr Gly Pro Ser
            275                 280                 285

Glu Glu Gly His Glu Ala Ala Pro Glu Phe Thr Phe His Val Glu Ile
            290                 295                 300

Lys Ala Ser Ala Pro Lys Glu Gln Asp Leu Glu Gly Ala Thr Val Val
305                 310                 315                 320

Gly Ala Pro Ala Glu Gln Lys Ala Arg Gly Pro Ser Val Gly Lys
            325                 330                 335

Gly Thr Lys Glu Ala Ser Leu Leu Glu Pro Thr Asp Lys Gln Pro Ala
            340                 345                 350

Ala Gly Leu Pro Gly Arg Pro Val Ser Arg Val Pro Gln Leu Lys Ala
            355                 360                 365

Arg Val Ala Gly Val Ser Lys Asp Arg Thr Gly Asn Asp Glu Lys Lys
            370                 375                 380

Ala Lys Gly Ala Asp Gly Lys Thr Gly Ala Lys Ile Ala Thr Pro Arg
385                 390                 395                 400

Gly Ala Ala Thr Pro Gly Gln Lys Gly Thr Ser Asn Ala Thr Arg Ile
            405                 410                 415

Pro Ala Lys Thr Thr Pro Ser Pro Lys Thr Pro Pro Gly Ser Gly Glu
            420                 425                 430

Pro Pro Lys Ser Gly Glu Arg Ser Gly Tyr Ser Ser Pro Gly Ser Pro
            435                 440                 445
```

-continued

```
Gly Thr Pro Gly Ser Arg Ser Arg Thr Pro Ser Leu Pro Thr Pro Pro
        450                 455                 460

Thr Arg Glu Pro Lys Lys Val Ala Val Val Arg Thr Pro Pro Lys Ser
465                 470                 475                 480

Pro Ser Ala Ser Lys Ser Arg Leu Gln Thr Ala Pro Val Pro Met Pro
                485                 490                 495

Asp Leu Lys Asn Val Arg Ser Lys Ile Gly Ser Thr Glu Asn Leu Lys
            500                 505                 510

His Gln Pro Gly Gly Gly Lys Val Gln Ile Ile Asn Lys Lys Leu Asp
        515                 520                 525

Leu Ser Asn Val Gln Ser Lys Cys Gly Ser Lys Asp Asn Ile Lys His
    530                 535                 540

Val Pro Gly Gly Gly Ser Val His Ile Val Tyr Lys Pro Val Asp Leu
545                 550                 555                 560

Ser Lys Val Thr Ser Lys Cys Gly Ser Leu Gly Asn Ile His His Lys
                565                 570                 575

Pro Gly Gly Gly Gln Val Glu Val Lys Ser Glu Lys Leu Asp Phe Lys
            580                 585                 590

Asp Arg Val Gln Ser Lys Ile Gly Ser Leu Asp Asn Ile Thr His Val
        595                 600                 605

Pro Gly Gly Gly Asn Lys Lys Ile Glu Thr His Lys Leu Thr Phe Arg
    610                 615                 620

Glu Asn Ala Lys Ala Lys Thr Asp His Gly Ala Glu Ile Val Tyr Lys
625                 630                 635                 640

Ser Pro Val Val Ser Gly Asp Thr Ser Pro Arg His Leu Ser Asn Val
                645                 650                 655

Ser Ser Thr Gly Ser Ile Asp Met Val Asp Ser Pro Gln Leu Ala Thr
            660                 665                 670

Leu Ala Asp Glu Val Ser Ala Ser Leu Ala Lys Gln Gly Leu
        675                 680                 685
```

CONFORMATIONALLY ABNORMAL FORMS OF TAU PROTEINS AND SPECIFIC ANTIBODIES THERETO

The invention relates to Alzheimer's disease and to other tauopathies.

This application is a U.S. national phase application under 35 U.S.C § 371 of PCT Application No. PCT/EP02/00897 filed 29 Jan. 2002, which claims priority to Austrian Application No. A 175/2001 filed 2 Feb. 2001.

Alzheimer's disease (AD) is the most common chronic neurodegenerative disorder which is characterized clinically by a progressive and irreversible loss of cognitive and behavioral function. The disease can persevere for over 10 years, advancing from mild symptoms to extremely severe manifestations. AD afflicts approximately 10% of the population over the age of 65 and 20% of the population over the age of 80. As a result of growing of Western societies, the number of persons afflicted is rising: already there are five million sufferers in the USA alone and by the end of the year 2000, there will be roughly 18 million people with dementia in the world. Of these, it is thought, that about two third of cases, i.e. 12 million, will be Alzheimer's disease. It is the fourth largest killer in the Western world after the heart diseases, cancer and strokes. The number of people with dementia is rising quickly. By 2025, there will be twice the number of people with dementia in the developed world as there were in 1980. The cost to the society for looking after the sufferers is enormous. For example, the costs to the US society for diagnosing and managing AD, primarily for custodial care, is currently estimated at US $80 billion annually. Currently, neither presymptomatic diagnostic test nor cure for AD is available. The disease is therefore clinically diagnosed after appearance of symptoms primarily by exclusion of other forms of dementia. Accumulation of the classical hallmarks, senile (neuritic) plaques and neurofibrillary tangles (NFT) in the AD brains, observed 93 years ago by the Bavarian psychiatrist Alois Alzheimer in 1907, still remain the neuropathological characteristic of AD.

The common denominator of intracellular neurofibrillary structures (neurofibrillary tangles, dystrophic neurites, and neuropil threads) are paired helical filaments (PHFs). The major protein subunit of the PHFs is microtubule associated protein tau in abnormally hyperphosphorylated form (Grundke-Iqbal et al., 1986; Wischik et al., 1988 a,b). Neurons with neurofibrillary changes degenerate, and the degree of this degeneration directly correlates with the degree of dementia in the affected individuals (Blessed et al., 1968).

Normal tau is a microtubule associated protein that distributes mainly to axons. Tau protein is taking part in modulating the assembly, spatial organization and behavior of microtubules (MT) in neurons and probably glial cell bodies (Drewes et al., 1998; Drubin and Kirschner, 1986; Lo-Presti et al., 1995). Tau proteins are encoded by a single gene located on chromosome 17, but are detected as multiple isoforms in tissue extracts from adult brains (Goedert et al., 1989; Himmler A., 1989; Kosik et al., 1989). Heterogeneity of tau proteins is in part due to alternative splicing, giving rise to six isoforms in the adult human brain. These distinct isoforms differ by the presence or absence of 29- or 58-amino acid inserts in the amino-terminal region and by the addition or deletion of a tandem repeat (which can be repeated either 3 or 4 times) in a carboxy-terminal region of tau referred to as microtubule binding domain. This region is composed of imperfect repeats of 31 or 32 amino acid residues. In humans, the smallest tau isoform contains 352 amino acid residues with three tandem repeats in the MT-binding domain and no amino terminal inserts, whereas the largest isoform contains 441 residues with four repeats and both amino terminal inserts. For simplicity, all numbering in this patent application refers to the longest human tau protein isoform, htau40, containing all inserts (441 amino acid long) according to Goedert et al. (1989).

A number of neurological diseases are known to have filamentous cellular inclusions containing microtubule associated protein tau e.g. Alzheimer's disease (AD), progressive supranuclear palsy (PSP), corticobasal degeneration (CBD), Pick's disease (PiD) and a group of related disorders collectively termed frontotemporal dementia with Parkinsonism linked to chromosome 17 (FTDP-17), amyotropic lateral sclerosis (ALS), Creutzfeldt-Jakob disease (CJD), dementia pugilistica (DP), Gerstmann-Straussler-Scheinker disease (GSSD), Lewy body disease and Huntington disease (Dickinson et al., 1998; DiFiglia et al., 1997; Forno, 1986; Hirano and Zimmerman, 1962; Nishimura et al., 1995; Prusiner 1996; Reed et al., 1998; Roberts, 1998; Schmidt et al., 1996; Shankar et al., 1989; Spillantini et al., 1998). Although the etiology, clinical symptoms, pathologic findings and the biochemical composition of inclusions in these diseases are different, there is emerging evidence suggesting that the mechanisms involved in aggregation of normal cellular proteins to form various filamentous inclusions are comparable. It is believed, that an initial alteration in conformation of microtubule associated protein tau, that initiates generation of nuclei or seeds for filament assembly, is a key feature. This process can be influenced by the posttranslational modification of normal proteins, by mutation or deletion of certain genes and by factors that bind normal proteins and thus alter their conformation. The tau protein is very hydrophilic. It can be readily extracted from brain tissue or cultured cells. In comparison, filamentous tau extracted from Alzheimer's diseased brain tissues is relatively insoluble. Besides phosphorylation, insoluble and normal soluble tau differ in the extent of posttranslational modifications, which include glycosylation, glycation, ubiquitination and racemization (Kenessey et al., 1995; Ko et al., 1999; Mori et al., 1987; Wang et al., 1996; Yan et al., 1994).

The mechanism by which tau protein is modified to take part in filament formation in AD is unknown. Tau is one of the most soluble proteins known (Cleveland 1977 a,b; Lee et al. 1988) and therefore its aggregation in AD is particularly enigmatic. Phosphorylation of tau affects the potential of tau to form aggregates, producing either stimulatory or inhibitory effects, presumably depending on the site of phosphorylation (Crowther et al., 1994; Schneider et al., 1999). Many in vitro studies demostrate that in the presence of the reducing agent, dithiothreitol (DTT), unsaturated free fatty acids, RNA or glycosaminoglycans, normal tau can be transformed into filaments (Goedert et al., 1996; Kampers et al., 1996; Perez et al., 1996; Wilson and Binder, 1997). Furthermore, the process of filament formation can also be accelerated by the presence of cross-linked tau generated through oxidation at Cys322 (Schweers et al., 1995). The parameters that have been varied in different filament assembly studies have included tau protein concentration, pH, and ionic strength of the incubation is many fold higher than exists in the cytoplasm under physiological conditions. Examination of in vitro formed tau filaments by scanning transmission electron microscopy (STEM) showed that these filaments differ from native paired helical filaments (Ksiezak-Reding, 1998). In the absence of glycans or RNA, no PHF-like filaments are detectable in samples containing unphosphorylated or phosphorylated wild type tau; normal tau. Studies of chemically cross-linked, heparin treated tau indicate that heparin treatment induces conformational change in tau protein (Paudel and Li, 1999). Taken together the in vitro data suggest (a) that the microtubule binding domain is important for assembly of tau filaments; and (b) that formation of tau filaments requires conformational change(s) of tau. Simultaneously these studies show that none of tau modifications described, are alone capable to induce filamentous tau formations that correlate with clinical expression of Alzheimer's disease. Identification and description of factors important for the initiation of tau changes leading to filament formation in disease conditions would be important for the development of presymptomatic diagnostic markers and therapeutic agents to interfere the progression of tauopathies.

An object of the present invention is therefore to provide a reliable drug target for early therapeutic intervention in Alzheimer's disease and other tauopathies. Furthermore it is desired to provide a specific monoclonal antibody capable of specific detection and interaction with this drug target. This antibody should not only be suitable for presymtomatic detection of the molecule but for inhibition and elimination of this molecule as well, hence being suitable for presymtomatic diagnosis, treatment and prevention of Alzheimer's disease and other tauopathies.

These objects are addressed with the present invention which relates in one aspect to an antibody with a specificity to abnormal forms of tau protein which are conformationally different from normal tau, said antibody being non-specific for a normal tau protein. Such abnormal forms of tau proteins represent a novel family of molecules, intra- and extra-neuronally located soluble and insoluble, preferably abnormally truncated, forms of tau proteins, which are conformationally different from normal tau (Novak et al., 1991, 1993). It could be shown with the present invention that these conformationally different forms of tau proteins—which are called "tauons" within the present specification—are seeds, nucleation centers in a self-propagating process of filamentous tau formations that is correlative to clinical expression of Alzheimer's disease thus tauons are important therapeutic targets for Alzheimer's disease. The tauons according to the present invention may be abnormally truncated tau proteins. Biological activity of tauons can be inhibited in vitro and inside of neurons by the antibodies according to the present invention. These antibodies have a capacity to stain presence of tauons in presymtomatic stages I, II and III of AD, which makes them suitable for presymtomatic diagnosis of this disease. It is critical for the antibodies according to the present invention that only the conformationally different form of tau protein (i.e. the "tauon") is recognized by this antibody whereas the normal tau protein does not bind to the antibodies according to the present invention.

Within the course of the present invention AD truncated forms of microtubule associated protein tau were purified to homogenity and shown to be a major part of filamentous tau isolations from Alzheimer's diseased neurons. The amino acid sequence data indicated that the backbone of tauons is indistinguishable from that of protein tau but tauons could be distinguished immunologically from normal human tau by the different conformation as revealed by the conformation specific monoclonal antibodies according to the present invention. Specific examples for such antibodies are the monoclonal antibody DC-11 which is produced by the hybridoma cell line which was deposited in the European Collection of Cell Cultures (ECACC) under deposit No. 00082216 and monoclonal antibody DC-11/I which is produced by the hybridoma cell line DC-11/I and was deposited in the ECACC under deposit No. 00082215. This family of monoclonal antibodies which is provided with the present invention is defined by recognition of tauon-specific conformation without recognizing normal human soluble tau. The different conformation compared to normal human tau, was attributed pathologically to abnormal truncation at the N-terminus or at the C-terminus or at both termini of tau molecule in the samples tested so far from Alzheimer's disease patients. Interestingly, the different conformation was regardless of tau isoform and level of phosphorylation. The indispensable pathological requirements for tauons to attain typical conformation is presence of prolin rich and microtubule binding domains and truncated flanking region(s). Furthermore tauons could be distinguished from normal human tau by their pathological activities, namely that tauons represent a seed, nucleation center, that initiates tau aggregation and tauons disassemble microtubules assembled from normal tau and tubulin. Tauons preincubated with antibodies according to the present invention, especially monoclonal antibodies of the DC-11 family, showed no diassemble capacity or assembled microtubules from normal tau and tubulin. Moreover, tauons cause upon microinjection to differentiated human neurons significant displacement of endogenous tau from microtubule bound tau fraction, retraction of neuronal processes and degeneration of the cells. If tauons are microinjected together with monoclonal antibodies according to the present invention, no neurodegenerative changes were observed in differentiated neurons. This shows that the antibodies according to the present invention, especially the DC-11 monoclonal antibodies, inhibit tauons activity intraneuronally and therefore could be used as intracellular drugs (for example as therapeutic intracellular antibodies, intrabodies). Immunohistologically, as seen with the antibodies according to the present invention, tauons occur already in presymptomatic stages I, II and III in pre-α-neurons, in both the transenthorinal and enthorinal region of AD, therefore, after proper coupling of tracers, antibodies according to the present invention could be used for intravital presymptomatic diagnosis for AD.

Preferably, the antibody according to the present invention exhibits a specificity of at least 50%, preferably at least 90% to the conformationally different form of tau ("tauon") compared to the antibody DC-11. Specificity may be tested by any standard test available for detecting antibody's specificity, e.g. ELISA tests, radioimmuno-assays, atomic force microscopy with cantilever-bound binding partners, etc.

Generally, all antibodies which are specifically reactive with the conformationally different tau protein, especially abnormally truncated forms thereof, but not with normal soluble tau are also included within the scope of the present invention.

Preferably, the antibody according to the present invention is said to be "specifically reactive" with a molecule if it is capable of binding with a molecule to thereby couple the molecule to the antibody. The term "epitope" is meant to refer to that portion of an antigen which can be recognized and bound by an antibody. An antigen may have one or more than one epitope. An "antigen" is capable of inducing an animal to produce antibody capable of binding to an epitope of that antigen. The specific reaction referred to above is meant to indicate that the antigen will immunoreact, in a highly selective manner, with its corresponding antibody and not with the multitude of other antibodies which may be evoked by other antigens.

Especially preferred antibodies according to the invention are derived from deposited hybridoma cell lines DC-11 (ECACC deposit No. 00082216) and DC-11/I (ECACC deposit No. 00082215) exhibit high specificity and selectivity and will react with conformationally different form of tau ("tauon"), but not with normal soluble tau. Specificity may be tested by any standard test available for detecting antibody's specificity, e.g. ELISA tests, radioimmuno-assays, etc.

"Antibody" as used herein is meant to include intact molecules and fragments thereof as well as synthetic and biological derivatives thereof, such as for example Fab, F(ab')$_2$ an F$_V$ fragments-free or expressed e.g. on the surface of filamentous phage on pIII or pVIII or other surface proteins, or on the surface of bacteria, which are capable of binding an antigen. Fab, F(ab')$_2$ and F$_V$ fragments lack the F$_C$ fragments of intact antibody, clear more rapidly from the circulation and may have less non-specific tissue binding of antibody. Furthermore F$_V$ antibody (often called as minibody) can be easily engineered to carry on its C-terminus specific tracer and used for early intravital presymtomatic diagnosis of AD, since stage I, II and III of AD that is recognized by the antibodies according to the present invention is not associated with intellectual decline.

Within the present invention, monoclonal antibodies or monoclonal antibody fragments are preferred. Therefore, according to another aspect the present invention also relates to hybridoma cell lines producing a monoclonal antibody according to the present invention.

The term "tau" as used in the present application refers to the longest isoform of human microtubule associated protein tau containing all alternatively spliced inserts as described in M. Goedert et al., 1989.

According to another aspect of the present application the invention relates to an abnormally truncated form of tau protein which is a conformationally different form of tau protein, said conformationally different form of tau protein specifically recognizeable by an antibody according to the present invention.

Accordingly, the present invention is drawn to a novel family of molecules intra- and extraneuronally located soluble and insoluble abnormally truncated form of tau proteins which are conformationally different from normal tau and are called "tauons".

"Tauons" therefore are conformationally different forms of tau protein which are specifically recognized by the antibodies according to the present invention. Tauons useful in the present invention comprise the sequence according to SEQ ID No:1 and may be flanked by further amino acids (see SEQ ID NO:2 and SEQ ID NO:3). The tauons conveniently are in the range from about 100 to 400 amino acids and represent truncated forms of tau protein in this range. The tauons according to the present invention may be abnormally truncated at the N- or C-terminus or at both termini (see FIGS. 2-13). The term "abnormally truncated" as used herein refers to tau peptides ("tauons") identified in diseased neurons in AD with tauon specific monoclonal antibodies provided with the present invention.

Abnormally truncated forms of human tau proteins—tauons—can be prepared by using any of numerous well known synthetic recombinant techniques. Briefly, most of the techniques which are used to transform cells, construct vectors, extract messenger RNA, prepare cDNA libraries, and the like are widely practiced in the art, and most practitioners are familiar with the standard resource materials which describe specific conditions and procedures. However, for convenience, the following paragraphs may serve as a guideline.

The most commonly used prokaryote system for the production of recombinant proteins remains *E. coli*, however, other microbial strains may also be used, such as Bacilli, for example *Bacillus subtilis*, various species of Pseudomonas or other bacterial strains. In such prokaryotic systems, plasmid vectors which contain replication sites and control sequences derived from a species compatible with the host are used. Commonly used prokaryotic control sequences include promoters for transcription initiation, optionally with an operator, along with ribosome binding site sequences.

A wide variety of eukaryotic hosts are also now available for production of recombinant foreign proteins. As in bacteria, eukaryotic hosts may be transformed with expression systems which produce the desired protein directly, but more commonly, signal sequences are provided to effect the secretion of the protein. Eukaryotic systems have the additional advantage that they are able to process introns which may occur in the genomic sequences encoding proteins of higher organisms. Eucaryotic systems also provide a variety of processing mechanisms which result in, for example, glycosylation, oxidation or derivatization of certain amino acid residues, conformational control, and so forth.

Commonly used eukaryotic systems include yeast, insect cells, mammalian cells, avian cells, and cells of higher plants. The list is not exhaustive. Suitable promoters are available which are compatible and operable for use in each of these host types as well as are termination sequences and enhancers, as e.g., the baculovirus polyhedron promoter. As above, promoters can be either constitutive or inducible. For example, in mammalian system, the MTII promoter can be induced by the addition of heavy metal ions.

The particulars for the construction of expression systems suitable for desired host are known to those in the art. For recombinant production of the protein, the DNA encoding it is suitable ligated into the expression system of choice, and the system is then transformed into the compatible host cell which is then cultured and maintained under conditions wherein expression of the foreign gene takes place. The tauons of this invention produced this way, are recovered from the culture, either by lysing the cells or from the culture medium as appropriate and known to those in the art.

Correct ligations for plasmid construction can be confirmed by the first transforming a suitable host with the ligation mixture. Successful transformants are selected by ampicillin, tetracycline or other antibiotic resistance or using other markers depending on the mode of plasmid construction, as is understood in the art.

The present invention therefore relates to a preparation of tauons, especially from human or recombinant resources, being essentially free of other proteins, especially from normal tau proteins. Such preparations may be provided by procedures involving an immunoaffinity step using the antibodies according to the present invention. Preferably, the preparation according to the present invention contains more than 80% tauons, especially more than 95% tauons, of total protein.

Further the present invention also relates to a kit for detecting tauons, abnormally truncated forms of tau protein, which are conformationally different from normal tau in a sample of Alzheimer's disease brain tissue or in a sample of a body fluid comprising an antibody according to the present invention and a suitable container for providing the sample. It is possible to provide the antibodies in a kit for detecting or isolating of tauons. With the help of antibodies according to the present invention tauon proteins may be detected and isolated from various sources including Alzheimer's diseased neurons of transenthorinal, enthorinal region and hippocampus. Tauons isolated in this way may be further used as immunogen for immunization e.g. of mice for construction of hybridomas producing specific monoclonal antibodies against tauons not recognizing normal full length tau. This method comprises identifying and releasing neurons from transenthorinal, enthorinal and hippocampal region of Alzheimer's diseased brain tissues into the solution preserving abnormal conformation of tauons.

After preparation and purification, tauons are used as immunogens and injected subcutaneously to mice in monthly intervals. Spleens from these animals are used for construction of hybridomas producing monoclonal antibodies against tauons. These can be produced using well-established hybridoma techniques first introduced by Köhler and Milstein (see M. Köhler and C. Milstein, "Continuous Cultures of Fused Cells Secreting Antibody of Pre-Defined Specificity", Nature, 256, pp. 495-497, 1975). After a sufficient long immunization, antibody-producing lymphocytes are obtained from the animal either from the spleen, lymph nodes or peripheral blood. Preferably, the lymphocytes are obtained from the spleen. The splenic lymphocytes are then fused with a myeloma cell line, usually in the presence of a fusing agent such as polyethylene glycol (PEG). Any of number of myeloma cell lines may be used as a fusion partner according to standard techniques; for example the P3-NS1/1-Ag4-1, P3-x63-Ag8.653 myeloma lines. The resulting cells, which include the desired hybridomas, are then grown in a selective medium, such as HAT medium, in which unfused parental myeloma or lymphocyte cell eventually die. Only the hybridoma cells survive and can be grown under limiting conditions to obtain isolated clones. The supernatants of the hybridomas are screened for the presence of antibody of that desired specificity, e.g. by immunoassay techniques using the antigen that had been used for immunization. Positive clones can then be subcloned under limiting dilution condition or on soft agar and the monoclonal antibody produced can be isolated. Hybridomas produced according to these methods can be propagated in vitro or in vivo (in ascites fluid) using techniques known in the art. Commonly used methods for purfying monoclonal antibodies include ammonium sulphated precipitation, ion exchange, chromatography, and affinity chromatography (see e.g., H. Zola et al., "Techniques for the Production and Characterization of Monoclonal Antibodies", in Monoclonal Hybridoma Antibodies: Techniques and Applications, J. G. R. Hurell (ed.), pp. 51-52 (CRC Press 1982)).

Preferably, the kit according to the present invention further contains means for detecting the binding event of said antibody binding to said conformationally different tau protein. Preferably secondary antibodies especially secondary antibodies which are specifically labeled. Also the magnetic beads technology may be used within the scope of the present invention as well as other protein identifying methods using antibodies. The method comprises identifying in a test sample from the person, tauon, which is abnormally truncated tau protein. "Test sample" as used herein refers to biological sample from the person that is suspected of containing tauons. Test sample can comprise brain tissue having abnormally truncated tau proteins, such as hippocampal tissue or frontal cortex tissue or, the test sample can comprise cerebrospinal fluid (CSF). In a preferred embodiment, the test sample comprises CSF and the protein identified is CSF-tauon. Identification of abnormally truncated tau proteins—tauons—conveniently comprises indentifying in the test sample antigens capable of binding with antibodies specifically reactive with abnormally truncated tau proteins—tauons—comprising the sequence (SEQ ID NO:1) and flanked by amino acids such that said tauons are in range from about 100 to 400 amino acids in length and characterized by tauon specific conformation different from normal soluble protein tau, or antibodies specifically reactive with abnormally truncated tau proteins—tauons—comprising the sequence (SEQ ID NO:1) and flanked by amino acids such that said tauons are in range from about 100 to 400 amino acids in length and characterized by tauon specific conformation different from normal soluble protein tau. The presence of a tauon indicates a disease associated with the accumulation of the tauons in AD patients and other sufferers with tauopathies.

A further aspect of the present invention relates to a method for detecting an abnormally truncated form of tau protein which is conformationally different from normal tau in a body fluid of a patient comprising mixing said body fluid with an antibody according to the present invention, detecting the presence of a binding event between the antibody and the conformationally different tau protein (tauon) and optionally measuring the amount of conformationally different tau protein being bound to said antibody. The presence of a tauon indicates a disease associated with the accumulation of the tauons in a person including AD and other tauopathies. The body fluid of a patient may be any biological test sample from a person that is suspected of containing tauons. This body fluid can comprise brain tissue such as hippocampal tissue or frontal or a cortex tissue or cerebrospinal fluid (CSF). In a preferred embodiment the body fluid comprises CSF and the protein identified is CSF-tauons.

This identification of tauons can conveniently be acomplished by biochemical or cytochemical means or by enzyme immunoassays such as decribed in many manuals of immunoassay producers as it is understood in the art. When biochemical means are used preferably 0.01 to 10 g, especially 0.5 to 1 g, of tissue containing diseased tau protein is used, run on a gel and identified by Western blot. Such a technique is believed do be adequate in the absence of age matched controls which have been shown to be non-reactive with the antibodies according to the present invention. Cytochemical means, staining, has shown no reactivity with normal tissue.

CSF from patients with AD and patients with non-AD neurological diseases as well as normal subjects were surveyed by ELISA to quantitate level of tauons. The CSF tauon level was significantly increased in AD patients as compared with that with patients with non AD neurological diseases and controls. In AD, the significant increase was found irrespective of age of onset, apolipoprotein E genotype and clinical stage. Western blots of AD CSF proteins reveal several immunoreactive bands with apparent molecular weight between 50 and 15 kD consistent with abnormally truncated tau proteins. These results indicate that CSF-tauons reflect that progressive accumulation of diseased tau caused by progression of AD.

According to a further aspect the antibodies according to the present invention may be used for the preparation of drug for the treatment of Alzheimer's disease patients. The antibodies may be biotechnologically modified into single chain molecules equipped with targeting sequence able to deliver them into the neuroblastoma cells expressing tauons. Inside of the present AD cellular model, antibodies bind tauons and interfere with their pathological effects (sequestration of normal tau) and increase the degradation of abnormally truncated forms of tau protein. In vitro assays (sequestration of tau protein, filament assembly, microtubule disassembly) with abnormally truncated tau proteins and their correlation with severity of Alzheimer's disease show that they are important drug targets.

The present invention will be described in more detail by the way of the following examples and the figures to which the invention should not be limited.

FIG. 1 shows an overview of the tauon preparation;

FIG. 2 shows a summary schematic representation of tauon amino acid sequences;

FIG. 3 shows minimal tauon;

Figure 6:
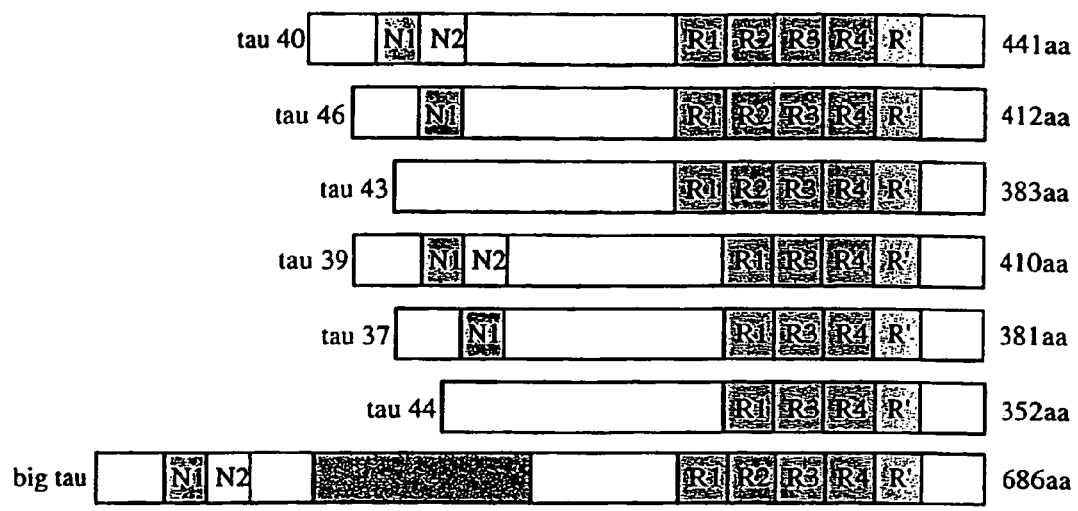

FIG. 4 shows C-terminally truncated tauon;
FIG. 5 shows N-terminally truncated tauon;
FIG. 6 shows a schematic tau representation;
FIG. 7 shows human tau 37;
FIG. 8 shows human tau 39;
FIG. 9 shows human tau 40;
FIG. 10 shows human tau 43;
FIG. 11 shows human tau 44;
FIG. 12 shows human tau 46; and
FIG. 13A and FIG. 13B show rat big tau.

EXAMPLES

Example 1

Preparation of the Monoclonal Antibodies of DC 11 Family Specific for Tauons

Preparation of Soluble and Insoluble Tauons as Antigens for Immunization (FIG. 1)

For isolation of tauons from human AD brains, a new approach was developed which is partially based on the methods described by Kopke et al., (1993) and Greenberg and Davies (1990). Human brains, showing changes characteristic for I.-III. Braak's stage of AD with short post mortem delay (PMD) were selected. Blocks of the temporal lobe including the enthorinal and transenthorinal regions, amygdala and hippocampal region were selected. The tissue was dissected and immediately immersed into minimal essential medium (Gibco). Tissue was finely minced and pushed through a 150 µm mesh wire screen. At this stage the brain sample was divided into two aliquots: sample A and sample B.

Sample A was further processed in 20 mM TRIS, pH 8, 0.32 M sucrose, 10 mM β-mercaptoethanol, 5 mM EGTA, 1 mM EDTA, 5 mM $MgSO_4$, 5 mM benzamidine, 10 mM glycerolphosphate, 6 mM phenylmethylsulfonyl fluoride, 50 mM sodium fluoride, 5 µg/ml leupeptin, 1.5 µg/ml pepstatin and 2 µg/ml of aprotinin and centrifuged at 25 000×g for 35 min at 4° C. to remove cellular debris. The supernatant was then pelleted at 200 000×g for 40 min. The resulting pellet was extracted with 8 M urea at room temperature for 70 min and spun at 300 000×g for 45 min at room temperature. The supernatant was dialysed for 24 hrs against the 10 mM TRIS pH 7.6 with frequent changes and then dialysed for 24 hrs against 100 mM MES, 0.5 mM $MgCl_2$, 1 mM EDTA, 2 mM EGTA, 1 mM dithiotreithol, 0.75 mM NaCl, 0.1 mM phenylmethylsulfonyl fluoride and 50 mM NaF, pH 2.7. The precipitated proteins were removed by centrifugation at 200 000×g for 40 min. The 200 000×g supernatant was dialyzed against 25 mM MES, pH 6.4, 0.5 mM $MgCl_2$, 0.1 mM EDTA and 1 mM dithiotreithol and subsequently fractionated on Cellulose Phosphate column which was equilibrated with the same buffer. The column was loaded with 2 mg/ml of proteins and eluted with 20 ml of linear gradient of NaCl (0-1M) in equilibrating buffer. The proteins eluted with 0.1-0.8 M NaCl were evaluated by Western blotting and concentrated by speed vacuum apparatus.

Sample B was put into 10 volumes of cold buffer (10 mM TRIS, 1 mM EGTA, 0.8 M NaCl, 10% sucrose, pH 7.4) in a glass homogenizer. After centrifugation at 27 000×g for 30 min at 4° C., the supernatant was saved and the pellet was homogenized with the buffer and centrifuged at 27 000×g for 30 min. The 27 000×g supernatants from both centrifugations were combined, adjusted to 1% (wt/vol) N-lauroylsarcosine and 1% (vol/vol) β-mercaptoethanol and incubated at 37° C. for 3 hrs on shaker. After centrifugation at 35 000 rpm for 30 min, the pellet was homogenized in 5 ml of homogenizing buffer supplemented with 1% mercaptoethanol and filtered through 0.45 µm filter. The filtrate was centrifuged at 35 000 rpm for 1 hr. The pellet was resuspended in 50 mM Tris, pH 6.8 and extracted with 2.5% formic acid for 2 min and then centrifuged at 10 000×g for 10 min to pellet insoluble material. The supernatant was dialysed overnight at 4° C. against 10 mM Tris, pH 7.4 and centrifuged as previously. The resulting supernatant (fraction II) was concentrated using speed vacuum apparatus and evaluated by SDS-PAGE followed by Western blotting. Pellet from the sample B after extraction with 2.5% formic acid containing insoluble tauons (fraction III) was saved and used for immunizations and dot assay. Tauons from fractions (I, II and III) were pooled and used as antigens (see FIG. 1) for immunization of mice.

Preparation of Hybridomas Producing Family of DC-11 Monoclonal Antibodies

Six weeks old Balb/c mice were divided into three groups, (A,B,C). The first two groups (A,B) were primed with 50 µg of antigen in complete Freund's adjuvant (Sigma) and boosted five times at three weeks intervals with 50 µg of the same antigen (Ag) in incomplete Freund's adjuvant. In the group A all doses were injected into foot pad and in the group B doses of Ag were administered subcutaneously. The third group of mice was injected only with one dose directly into the spleen in PBS (intrasplenic immunization) and one week after such priming were spleens used for fusion. Three days before the fusion, mice in group A and B were injected intravenously with 50 µg of immunogen in PBS. Spleen cells from immunized mice were fused with NS/0 myeloma cells according to the method of Kontsekova et al., 1988. $10^8$ splenocytes were mixed with $2×10^7$ NS/0 myeloma cells (ratio 5:1) and fused for 1 minute in 1 ml of 50% PEG 1550 (Serva) in serum free Dulbecco's modified Eagle's medium (DMEM) supplemented with 10% dimethyl sulphoxide. The fused cells were resuspended in DMEM containing 20% horse serum, L glutamine (2 mM), hypoxanthine (0.1 mM), aminopterin (0.004 mM), thymidine (0.016 mM) and gentamycin (40 U/ml) at a density of $2.5×10^5$ spleen cells per well on 96-well plates. Cells were incubated 10 days at 37° C. and growing hybridomas were screened for the production of anti-tauon specific monoclonal antibodies by ELISA and by immunohistochemistry.

Anti Tauons Antibody Screening by ELISA

ELISA was used to detect monoclonal antibodies in hybridoma culture supernatants which were directed against tauons. As a solid phase tauons prepared as described above with a following modification were used. Pool of the speed vacuum concentrated tau from fractions was separated by electrophoresis on polyacrylamide gel and truncated forms of tau protein were recovered by electroelution according to the method by Donofrio et al., (1986) and evaluated by SDS-PAGE. Microtiter plates were coated overnight with abnormally truncated tau proteins (10 µg/ml, 50 µl/well) at 4° C. in PBS. After blocking with 1% nonfat dried milk to reduce nonspecific binding, the plates were washed with PBS-0.05% Tween 20 and incubated with 50 µl/well of culture supernatant for 1 hr at 37° C. Bound monoclonal antibodies were detected with sheep anti-mouse Ig conjugated with horse radish peroxidase (DAKO). The reaction was developed with o-phenylenediamine solution as a peroxidase substrate and stopped with 50 µl 2 M $H_2SO_4$. Absorbance at 492 nm was measured using a Multiscan MCC/340 ELISA reader (Labsystems). Readings at least twice of the value of the negative controls were considered positive.

Positive cultures were further subcloned in soft agar according to the procedure of Kontsekova et al., 1991. Isolated subclones were re-screened for the production of specific anti-tauon monoclonal antibodies.

Immunohistochemical Screening of Anti Tauon Antibodies

Monoclonal antibodies identified as positive in anti-tauon ELISA and negative on normal tau, were re-screened on AD brain tissues for their specificity as follows:

The brains of patients with AD removed at autopsy were sectioned at 1 cm intervals in the coronal plate and stored at −20° C. The blocks of hippocampus, enthorinal, temporal, frontal, occipital and parietal cortex were fixed in 4% buffered paraformaldehyde at 4° C. for more than 4 days. Series of frontal sections (50 µm) were cut on vibratome and stored in PBS (pH 7.0) at 4° C. Free floating vibratome sections were pretreated for 2-3 min with 98% cold formic acid, incubated with pre-immune serum in PBS/Triton X 100. The serum used was from the same animal species as that of secondary antibody. Incubation of sections was done with the monoclonal antibody positive in ELISA (as described above) for 60 min at 37° C.

Incubation with the second biotinylated antibody (Vectastain Elite kit, Vector) was performed for 1 hr at room temperature. Immunoreactions were visualised with the avidin-biotin-peroxidase complex (Vectastain Elite kit, Vector) and 6 mg 3-3-diaminobenzidine-4HCl (SIGMA), 250 mg $NiCl_2$ (MERCK) in 10 ml 0.1 M acetate buffer (pH 6) with 100 µl $H_2O_2$. Reaction was terminated by washing the sections in PBS/Triton (Kiss et al., 1988; Cuello et al., 1993, Thorpe and Kerr, 1994)

Example 2

Quantitative Determination of the Abnormally Truncated Tau Proteins (Tauons) Using Family of DC-11 Monoclonal Antibodies Tauons were isolated as described above. The combination of monoclonal antibody DC 30 (recognizing both normal and pathological tau) and family of DC-11 monoclonal antibodies (specific for abnormally truncated tau) allows quantification of tauons in the tested samples prepared from AD-brains. Antibodies were purified from serum-free medium by protein A column chromatography. The wells of high-binding microtiter plate (Nunc) were coated with mixture of DC-11 monoclonal antibodies at a concentration of 10 µg/ml (50 µl/well) in PBS overnight at 4° C. Non-specific binding in wells was saturated by adding 200 µl of 1% nonfat dried milk in phosphate buffered saline (PBS) for 60 min at room temperature. The plates were washed 3 times with PBS-0.05% Tween 20 (v/v). The serially diluted standards containing recombinant tauons at concentrations ranging between 100-1000 µg/ml in PBS were added, as well as the test samples containing AD-tauons in amount of 50 µl. After incubation for 60 min at 37° C., plates were washed and the horse radish peroxidase conjugated antibody DC 3O diluted 1/5000 in PBS was added (50 µl/well) for 60 min at 37° C. After a final washing, 50 µl of orthophenylendiamine solution and 0.003% $H_2O_2$ were added to wells and plates were incubated in dark for 20 min. The reaction was stopped with 50 µl of 2 M $H_2SO_4$. Absorbance at 492 nm was read in ELISA reader Multiscan MC344 (Labsystems, Finland).

The standard curve for recombinant tauons was constructed from the obtained values and the corresponding concentrations of tauons in tested samples were determined from the standard curve.

Example 3

Detection of Tauons by Western Blotting Using Monoclonal Antibody DC-11

Purified recombinant full-length human tau and abnormally truncated tau proteins—tauons, were loaded on 5-20% gradient SDS-polyacrylamide gels and run under denaturated conditions according to Laemmli (1970). After SDS-PAGE, the transfer on polyvinyl difluoride membrane (Milipore) was carried out in 10 mM CAPS buffer pH 12 for 1 hr at 350 mA with cooling. After blotting, the membrane was washed in PBS and blocked with 1% dried nonfat milk in PBS for 1 hr at room temperature. Transferred proteins were incubated overnight at 4° C. with monoclonal antibody DC-11. After washing with PBS-0.05% Tween 20 (v/v), rat anti-mouse immunoglobulin labeled with horse radish peroxidase was used at a dilution 1/1000 and incubated 1 hr at room temperature. The membrane was then washed four times in PBS-Tween 20, developed with substrate solution (12 mg 4-chloro-1-naphtol, 4 ml methanol, 16 ml PB, 0.03% v/v $H_2O_2$) and the reaction was stopped in $H_2O$. Results indicated, that the antibody DC-11 recognized solely abnormally truncated tau—tauons, by contrast the monoclonal antibody DC 30 is pan tau antibody recognizing universally all known tau isoforms from many species (human, monkey, cow, pig, rat, mouse), regardless of their state of postranslational modifications.

Example 4

Immunohistochemical Identification of Tauons

Monoclonal antibody DC-11 family are suitable for visualization of tauons in AD-brains in different types of the immunohistochemical procedures.

Light Microscopic Labeling

The brains of patients with AD removed at autopsy were sectioned at 1 cm intervals in the coronal plate and stored at −20° C. The blocks of hippocampus, entorhinal, temporal, frontal, occipital and parietal cortex were fixed in 4% buffered paraformaldehyde at 4° C. for more than 4 days. Series of frontal sections (50 µm) were cut on vibratome and stored in PBS (pH 7) at 4° C. Free floating vibratome sections were pretreated for 2 min with 98% cold formic acid, incubated with pre-immune serum in PBS/Triton X 100. The serum used was from the same animal species as that of secondary antibody. Incubation of sections was done with monoclonal antibody DC-11 for 60 min at 37° C. Incubation with the second biotinylated antibody (Vectastain Elite kit, Vector) was performed for 1 hr at room temperature. Immunoreactions were visualized with the avidin-biotin-peroxidase complex (Vectastain Elite kit, Vector) and 6 mg 3-3-diaminobenzidine-4HCl (SIGMA), 250 mg $NiCl_2$ (MERCK) in 10 ml 0.1 M acetate buffer (pH 6) with 100 µl $H_2O_2$. Reaction was terminated by washing the sections in PBS/Triton (Kiss et al., 1988; Cuello et al., 1993, Thorpe and Kerr, 1994).

Light Microscopic Double Labeling

Free floating vibratome sections were pretreated for 2-3 min with 98% cold formic acid, incubated with pre-immune serum in PBS/Triton X 100. The serum used was derived from the same animal species as that of secondary antibody. Sections were incubated with first peroxidase conjugated monoclonal antibody DC-11 at a dilution 1:1000 in blocking solution (5% horse serum, PBS, 0.1% Triton) for 60 min at 37° C., developed in 0.06% DAB, 0.01% $H_2O_2$ in PBS (pH 7.2). Reaction was terminated by washing the sections in PBS/

Triton. Incubation of the same sections with second monoclonal antibody was done for 60 min at 37° C. Incubation with the biotinylated antibody (Vectastain Elite kit, Vector) was performed for 1 hr at room temperature. The reaction was visualized with the avidin-biotin-peroxidase complex (Vectastain Elite kit, Vector) and 0.06% 3-3-diaminobenzidine-4HCl (SIGMA), 0.01% $H_2O_2$, 2.5% $NiCl_2$ (MERCK) in 0.1 M acetate buffer and was terminated by washing the sections in 0.1 M acetate buffer (Kiss et al., 1988; Cuello, 1993).

Counterstaining with Fast Cresyl Violet

After finishing immunohistochemical staining, the sections were placed on glass slides and put into thermostat for 60 min at 56° C. After incubation slides were immersed in destilled water for 5 min, stained in fast cresyl violet solution for 5-10 min at 4° C., rinsed in water, and transferred to 96% ethanol until most of the cresyl violet staining was removed, cleared in xylen, and mounted with Entellan.

Immunofluorescent Staining

Free floating vibratome sections (30 μm) were pretreated for 2 min with 98% cold formic acid, incubated with pre-immune serum in PBS/Triton X 100. Sections were incubated with first primary monoclonal antibody DC-11 for 60 min at 37° C. and then incubated for 30 min with a FITC-conjugated goat anti mouse secondary antibody (Immunotech) diluted 1:500 in PBS/Triton at room temperature according to standard methods used in the field. After washing with PBS, sections were incubated with TRITC-conjugated primary antibody for 60 min at 37° C. and mounted in 0.1% paraphenylendiamin/glycerol solution.

Example 5

Microtubule Assembly and Microtubule Binding Assays with Tauons

Tubulin Purification

Tubulin was isolated from fresh pig brains, obtained from the local slaughter house, by temperature dependend cycles of microtubule polymerisation and depolymerisation, followed by phosphocellulose (Watman P11 phosphocellulose) ion-exchange chromatography (Valee, 1986).

Microtubule Assembly Assay

Purified tauons (5 mM) were mixed with precleared purified tubulin (10 mM) and GTP (1 mM) in the assembly buffer (100 mM PIPES pH 6.9, 2 mM EGTA, 1 mM $MgSO_4$) at +4° C. This tubulin concentration is below the critical concentration for spontaneous assembly (Black, 1987). Samples were pipetted into quartz cuvettes preheated to 37° C. The change of turbidity was measured spectrofotometrically in thermostatically controlled spectrophotometer (LKB) and recorded as change of $OD_{350}$ in 10 s intervals for a period of 30 min.

Microtubule Binding Assay

Binding curves of tauons with microtubules were measured as described previously (Gustke, 1992). Purified tubulin was incubated at 37° C. in the presence of GTP (1 mM) and taxol (20 μM) in the binding buffer (100 mM PIPES pH 6.9, 1 mM EGTA, 1 mM $MgSO_4$, 1 mM DTT) for 10 min. Microtubules were stabilized by taxol which does not interfere with the binding of tauons or normal tau protein and other MAPs, respectively (Valee, 1986; Wallis, 1993) thus eliminating the effect of microtubule assembly. Tauons were added in concentrations 2.5 mM, 5 mM, 7.5 mM, 10 mM, 15 mM, 20 mM, respectively. After centrifugation for 35 min, 43 000×g, 37° C. the pellets were resuspended in P buffer (50 mM PIPES pH 6.9, 1 mM EGTA, 0.2 mM $MgCl_2$, 5 mM DTT, 500 mM NaCl). Supernatant and pellets were analyzed on SDS-PAGE gels (Laemmli, 1970), stained with silver (Bloom, 1987). The gels were scanned on HPScanJet (Hewlett-Packard) scanner and analysis performed on a Macintosh computer using the public domain NIH Image program (developed at the U.S. National Institutes of Health and available on the Internet at rsb.info.nih.gov/nih-image/). The band intensities were converted to concentrations using the method of internal standards and calibration curves.

Example 6

Preparation of Recombinant Tauons

Recombinant truncated forms of tau protein were prepared using "Erase a Base System" (Promega) according to the technical manual. The system is based on exonuclease III specific digestion of inserted DNA starting from 5'overhang. The rate of digestion was uniform at constant temperature. The tau gene was cloned into pET17b vector through NdeI-EcoRI restriction sites producing pET/T40. To the C-end of the gene was added KpnI restriction site and three stop codons in all three reading frames downstream of the KpnI site. The EcoRI enzyme leaves 5'ends overhanging, the substrate for exoIII. KpnI leaves 3'ends overhanging which are resistant to exoIII digestion. 1 μg of pET/T40 vector double digested with EcoRI, KpnI/NEB and ethanol precipitated were diluted in 20 μl 1×ExoIII buffer and digested by 80 u exoIII at 37° C./dig. rate 450 bases/minute. 2.5 μl samples were transferred after ExoIII addition at 30 s intervals into 7.5 μl S1-nuclease mix/ 1.5 u S1-nuclease for 1 sample on ice. The collected samples were incubated at room temperature for 30 min to remove remaining single stranded tails. Klenow DNA polymerase was used to make blunt ends. DH5alfa competent cells were transformed directly with ligation mixtures of the samples. The subclones were screened by PstI-XhoI restriction and appropriate constructs were sequenced using T7-primer in pET vector.

Expression, Purification and Quantification of Recombinant Tauons

Tauons were expressed in *E. coli* BL21 (DE3) (Studier, 1986). Single bacterial colonies were inoculated to 500 ml of LB AMP (LB medium, 100 μg/ml ampicillin). Bacterial cultures were grown at 37° C. on rotary shaker until their $OD_{600}$ reaches 0.6-0.8 and then induced by adding IPTG (0.4 mM final concentration). After 3 hrs the bacterial cells were pelleted by centrifugation at 5000 g for 15 min at 4° C. (Sigma 6K15, rotor 12 500), and pellet of the cells quickly frozen in liquid nitrogen and stored at −70° C. until further use. For cell lysate preparation, bacterial pellet was resuspended in buffer A: (20 mM PIPES pH 6.9, 50 mM NaCl, 1 mM EGTA, 1 mM $MgSO_4$, 2 mM DTT, 0.1 mM PMSF), the cells were disrupted by sonication on ice for 6 min and cell debris removed by centrifugation at 45 000 rpm, 15 min at +2° C. (rotor TLA-120.2, Beckmann Optima TLX). Supernatants were filtered through 0.22 μm filters (Millipore) and tauons were immediately purified by ion exchange chromatography on phosphocellulose (cellulose phosphate Whatman P11) column. After loading the sample the column was washed with 10 bed volumes of the buffer A. Tauons were eluted with 20 ml of a linear gradient of NaCl (50 mM-0.5 M) in the buffer A. The 1 ml fractions were collected and those containing proteins were identified on SDS-PAGE. Fraction containing tauons were pooled and dialysed against PBS 3×60 min at 4° C.

Aliquots from the dialysate were vacuum dried (SpeedVac) and stored at −20° C. Recombinant tauons were quantified by PAGE, using serially diluted bovine serum albumine (BSA) as mass standard markers. The gel was stained by Coomassie blue, dried and the intensity of BSA and tau bands was calculated using Scion Image (Beta 3b, Scion Corp.). The calibration curve for BSA was constructed and used for quantification of tauons.

Example 7

Isolation of Tauons from Human AD-Brain

For isolation of tauons from human AD brains a new approach partially based on the methods described by Kopke et al., (1993) and Greenberg and Davies (1990) was developed. Human brains, showing changes characteristic for I.-III. Braak's stage of AD with short post mortem delay (PMD) were selected. Blocks of the temporal lobe including the enthorinal and transenthorinal regions, amygdala and hippocampal region were selected. The tissue was dissected and immediately immersed into minimal essential medium (Gibco). Tissue was finely minced and pushed through a 150 µm mesh wire screen. At this stage the brain samples were divided into two aliquots: sample A and sample B.

Sample A was further processed in 20 mM TRIS, pH 8, 0.32 M sucrose, 10 mM β-mercaptoethanol, 5 mM EGTA, 1 mM EDTA, 5 mM $MgSO_4$, 5 mM benzamidine, 10 mM glycerolphosphate, 6 mM phenylmethylsulfonyl fluoride, 50 mM sodium fluoride, 5 µg/ml leupeptin, 1.5 µg/ml pepstatin and 2 µg/ml of aprotinine and centrifuged at 25 000×g for 35 min at 4° C. to remove cellular debris. The supernatant was then pelleted at 200 000×g for 40 min. The resulting pellet was extracted with 8 M urea at room temperature for 70 min and spun at 300 000×g for 45 min at room temperature. The supernatant was dialysed for 24 hrs against the 10 mM TRIS pH 7.6 with frequent changes and then dialysed for 24 hrs against 100 mM MES, 0.5 mM $MgCl_2$, 1 mM EDTA, 2 mM EGTA, 1 mM dithiotreithol, 0.75 mM NaCl, 0.1 mM phenylmethylsulfonyl fluoride and 50 mM NaF, pH 2.7. The precipitated proteins were removed by centrifugation at 200 000×g for 40 min. The 200 000×g supernatant was dialyzed against 25 mM MES, pH 6.4, 0.5 mM $MgCl_2$, 0.1 mM EDTA and 1 mM dithiotreithol and subsequently fractionated on Cellulose Phosphate column which was equilibrated with the same buffer. The column was loaded with 2 mg of proteins and eluted with a linear gradient of NaCl (0-1M) in equilibrating buffer. The proteins eluted with 0.1-0.8 M NaCl were evaluated by Western blotting and concentrated by speed vacuum apparatus.

Sample B was put into 10 volumes of cold buffer (10 mM TRIS, 1 mM EGTA, 0.8 M NaCl, 10% sucrose, pH 7.4) in a glass homogenizer. After centrifugation at 27 000×g for 30 min at 4° C., the supernatant was saved and the pellet was homogenized with the buffer and centrifuged at 27 000×g for 30 min. The 27 000×g supernatants from both centrifugations were combined, adjusted to 1% (wt/vol) N-lauroylsarcosine and 1% (vol/vol) β-mercaptoethanol and incubated at 37° C. for 3 hrs while shaking on shaker. After centrifugation at 35 000 rpm for 30 min, the pellet was homogenized in 5 ml of homogenizing buffer supplemented with 1% mercaptoethanol and filtered through 0.45 µm filter. The filtrate was centrifuged at 35 000 rpm for 1 hr. The pellet was resuspended in 50 mM Tris, pH 6.8 and extracted with 2.5% formic acid for 2 min and then centrifuged at 10 000×g for 10 min to pellet insoluble material. The supernatant was dialysed overnight at 4° C. against 10 mM Tris, pH 7.4 and centrifuged as previous. The resulting supernatant was concentrated using speed vacuum apparatus and evaluated by SDS-PAGE followed by Western blotting.

Example 8

Purification of Normal Tau from Human, Pig and Cow Brain Tissues

Tau was purified by the modification of the method of Lindwall and Cole., 1984. Brain tissue was homogenized (1 mg/ml) in 0.1 mM MES, 0.5 mM $MgCl_2$, 1 mM EGTA, 1 M NaCl pH 6.5 and centrifuged at 100 000×g at 4° C. for 90 min. The supernatant was made up to 0.5% (v/v) 2-mercaptoethanol, heated at 100° C. for 5 min and centrifuged at 20 000×g at 4° C. for 30 min. This second supernatant was brought to 45% saturation in $(NH_4)_2SO_4$ and centrifuged at 20 000×g as above and the resulting pellet was resuspended in MES buffer without NaCl. After precipitation with 2.5% (v/v) perchloric acid and a further centrifugation at 20 000×g the final supernatant was dialysed against 5 mM Tris, pH 7.4 overnight at 4° C.

Example 9

Sequestration and Aggregation of Normal Tau into Tangles of Filaments by Tauons

Increasing amounts of normal tau (5-100 µg/100 µl) were mixed with fixed amount of tauons isolated from fraction I (10 µg/100 µl). The reaction was performed in a final volume of 100 ml of binding buffer (100 mM MES pH 7.6 containing 2 mM EGTA, 2% bovine serum albumin, 0.5 mM $MgCl_2$, 1 µM aprotinin and 20 µM leupeptin). The mixture was allowed to interact for 45 min at room temperature, then overlaid on 150 µl of 80% sucrose in the binding buffer and centrifuged for 1 hr at 100 000×g. The top 150 µl was removed and the remainder was sonicated for determining of interaction between tauons and normal tau by radioimmuno-dot-blot assay. The presence of tau in the sucrose layer indicates sequestration of healthy tau by tauons.

Example 10

Inhibition of Neuron Degeneration by Family of DC-11 Monoclonal Antibodies

Neuronal blastoma cells and growth factor are plated on Petri dishes in triplicate. The first group received tauons only and the second one received tauons and the mixture of DC-11 monoclonal antibodies.

Detection of the Transfected Tauons by Immunofluorescence

Cells were permeabilized for 5 min at room temperature in 0.2% Triton X 100 containing 80 mM PIPES, 1 mM $MgCl_2$, 1 mM EGTA, pH 6.6. Fixation of the cells was performed in 2% paraformaldehyde in the same buffer for 15 min on ice. Tauons were detected by indirect immunofluorescence avidin rhodamine detection system (Sigma).

Detection of Early Inhibition of Neuronal Differentiation

The cells were grown with the differentiation inducing factors. Level of differentiation was evaluated. The group of the cells harbouring tauons without antibodies had significantly impaired capacity to differentiate. However, group treated with mixture of tauons and antibodies differentiated to comparable level with the cells from control group treated with irrelevant protein.

REFERENCES

Black M M (1987) Comparison of the effects of microtubule-associated protein 2 and tau on the packing density of in vitro assembled microtubules Proc Natl Acad Sci USA 84: 7783-7787

Blessed G, Tomlison B E, Roth M (1968) The association between qualitative measaures of dementia and senile change in cerebral grey matter of elderly subjects. Br J Psychiatry 114: 797-811.

Bloom H, Beier H, Gross H S (1987) Improved silver staining of plant proteins, RNA and DNA in polyacrylamide gels. Electrophoresis 8: 93-99.

Cleveland D W, Hwo S Y, Kirschner M W (1977a) Psysical and chemical properties of purified tau factor and the role of tau in microtubule assembly. J Mol Biol 116: 227-247

Cleveland D W, Hwo S Y Kirschner M W (1977b) Purification of tau a microtubule-associated protein that induces assembly of microtubules from purified tubulin. J Mol Biol 116: 207-225

Crowther R A, Olesen O F, Smith M J, Jakes R, Goedert M (1994) Assembly of Alzheimer-like filaments from full-length tau protein. FEBS Letter 337:135-138

Cuello A C, Coté S L, Ribeiro-Da-Silva A (1993): Current protocols for light microscopy immunohistochemistry. Immunohistochemistry II John Wiley and sons Cichester, 148-167.

Dickson D W, Feany M B, Yen S -H, Mattiace L A; Davies P (1998) Cytoskeletal pathology in non-Alzheimer degenerative dementia: new lesions in diffuse Lewy body disease, Pick's disease, and corticobasal degeneration. J Neural Transm 47: 31-46

DiFiglia M, Sapp E, Chase K O, Davies S W, Bates G P, Vonsattel J P, Aronin N (1997) Aggregation of huntingtin in neuronal intra-nuclear inclusions and dystrophic neurites in brain, Science 277:1990-1993

Donofrio J C, Coonrod J D, Karathanasis V, Coelingh K V (1986) Electroelution for purification of influenza A matrix protein for use in immunoassay. 13: 107-120

Drewes G, Ebneth A, Mandelkow E M (1998) MAPs MARKs and microtubule dynamics. Trends Biochem Sci 23: 307-311

Drubin D G, Kirschner M W (1986) Tau protein function in living cells. J Cell Biol 103: 2739-2746

Forno L S (1986) The Lewy body in Parkinson's disease, In: Yahr M D, Bergmann K J (eds) Parkinson's Disease, Advances in Neurology, Vol. 45, Raven Press: New York pp. 35-43

Goedert M, Spillantini M G, Jakes R, Rutherford D, Crowther R A (1989) Multiple isoforms of human microtubule-associated protein tau: sequences and localization in Neurofibrillary tangles of Alzheimer's disease. Neuron 3: 519-526

Goedert M, Jakes R, Spillantini M, Hasegawa M, Smith M J, Crowther R A (1996) Assembly of microtubule-associated protein tau into Alzheimer~like filaments induced by sulfated glycosaminoglycans. Nature 383: 550-553

Greenberg S H, Davies P (1990) A preparation of Alzheimer paired helical filaments that displays distinct tau proteins by polyacrylamide gel electrophoresis. Proc Natl Acad Sci USA 87: 5827-5831

Grundke-Iqbal I, Iqbal K, Tung Y -C, Quinlan M, Wisniewski H M, Binder L I. (1986) Abnormal phosphorylation of the microtubule associated protein tau in Alzheimer cytoskeletal pathology. Proc Natl Acad Sci USA 83: 4913-17.

Gustke N, Steiner B, Mandelkow E M, Biernat J, Meyer H E, Goedert M, Mandelkow E (1992) The Alzheimer-like phosphorylation of tau protein reduces microtubule binding and involves Ser-Pro and Thr-Pro motifs. FEBS Lett 307: 199-205.

Himmer A (1989) Structure of the bovine tau gene: alternatively spliced transcripts generates a protein family. Mol Cell Biol 9: 1389-1396

Hirano A, Zimmerman H M (1962) Alzheimer's neurofibrillary changes. Arch Neurol 7: 73-88

Kampers T, Friedhoff P, Biernat J, Mandelkow E M, Mandelkow E (1996) RNA stimulates aggregation of microtubule-associated protein tau into Alzheimer-like paired helical filaments. FEBS Lett 399: 344-349

Kenessey A, Yen S -H, Liu W -K, Yang X -R, Dunlop D S (1995) Detection of D-aspartate in tau proteins associated with Alzheimer paired helical filaments. Brain Res 675: 183-189

Kiss A, Palkovits M, Skirboll L R (1988) Light microscopic triple-colored immunohistochemical staining on the same vibratome section using the avidin-biotin-peroxidase complex technique. Histochem 88: 353-356

Kopke E, Tung Y -Ch, Shaikh S, Alonso A C, Iqbal K, Grundke-Iqbal I (1993) Microtubule-associated protein tau abnormal phosphorylation of a non-paired helical filament pool in Alzheimer disease. J Biol Chem 268: 24374-24384

Kontseková E, Novák M, Kontsek P, Bornký L, Lesso J. (1988) The effect of postfusion cell density on establishment of hybridomas. Folia Biol (Praque) 34:18-22

Kontseková E, Novák M, Máciková I, Kontsek P. (1991) One-step method for establishing 8-azaguanine-resistant hybridomas suitable for the preparation of triomas. J Immunol Methods 145: 247-250

Kosik K S, Orecchio L D, Bakalis S, Neve R L (1989) Developmentally regulated expression of specific tau sequence. Neuron 2: 1389-1397

Ksiezak-Reding H, Yang G, Simon M, Wall J S (1998) Assembled tau filaments differ from native paired helical filaments as determined by scanning transmission electron microscopy STEM. Brain Res. 814: 86-98.

Laemmli U K (1970) Cleavage of structural proteins during the assembly of the head of bacteriophage T4. Nature 227: 680-685

Lindwall G, Cole R D (1984) The purifiction of tau protein and the Occurrence of two phosphorylation states of tau in brain. J Biol Chem: 259:12241-12245

Ko L W, Ko E C, Nacharaju P, Liu W K, Chang E, Kenessey A, Yen S H (1999) An immunochemical study on tan glycation in paired helical filaments. Brain Res 830:301-313

LoPresti P, Szuchet S, Papasozomenos S C, Zinkowski P R, Binder L I (1995) Functional implications for the microtubule-associated protein tau: localization in oligodendrocytes. Proc Natl Acad Sci USA 92:10369-10373

Mori H, Kondo J, Ihara Y (1987) Ubiquitin in a component of paired helical filaments in Alzheimer's disease. Science 235: 1641~1644

Nishimura T, Ideda K, Akiyama H, Kondo H, Kato M, Li F, Iseki E, Kosaka K (1995) Immunohistochemical investigation of tau-positive structures in the cerebral cortex of patients with progressive supranuclear palsy. Neurosci Lett 201: 123-126

Novák M, Kabát J, Wischik C M (1993) Molecular characterization of the minimal protease resistant tau unit of the Alzheimer's disease paired helical filament. J EMBO, Vol. 12, pp 365-370

Novák M, Jakes R, Edwards P C, Milstein C, Wischik C M (1991) Difference between the tau protein of Alzheimer paired helical filament core and normal tau revealed by epitope analysis of monoclonal antibodies 423 and 7.51. Proc Natl Acad Sci USA 88: 5837-5841

Paudel H, Li W (1999) Heparin-induced conformational change in microtubule-associated protein tau as detected by chemical cross-linking and phosphopeptide mapping. J Biol Chem 274: 8029-8038

Perez M, Valpuesta J M, Medina M, Montejo de Garcini E, Avila J (1996) Polymerization of tau into filaments in the presence of heparin: the minimal sequence required for tau-tau interaction. J Neurochem 67:1183-1190

Prusiner S B (1996) Human prion diseases and neurodegeneration. Curr Topics Microbiol Immunol 207:1-17

Reed L A Schmidt M L, Wszolek Z K, Balin B J, Soontomniyomkij V, Lee V M, Trojanowski J Q, Schelper R L (1998) The neuropathology of a chromosome 17-linked autosomal dominant parkinsonism and dementia ("pallido-ponto-nigral degeneration"). J Neumpathol Exp Neurol 57: 588-601

Roberts G W (1988) Immunocytochemistry of neurofibrillary tangles in dementia pugilistica and Alzheimer's disease: Evidence for common genesis. Lancet 2:1456-458

Schneider A, Bieeemat J, Von Bergen M, Mandelkow E, Mandelkow E M (1999) Phosphorylation that detaches tau protein from microtubules (Ser262, Ser214) also protects it against aggregation into Alzheimer paired helical filaments. Biochemistry 38: 3549-3558

Schweers O, Mandelkow E M, Biernat J, Mandelkow E (1995) Oxidation of cysteine-322 in the repeat domain of microtubule-associated protein tau controls the in vitro assembly of paired helical filaments. Proc Natl Acad Sci USA 92: 8463-8467

Shankar S K, Yanagihara R, Garruto R M, Grundke-Iqbal I, Kosik K S, Gajdusek D C (1989) Immunocytochemical characterization of neurofibrillary tan~Ies in amyotrophic lateral sclerosis and parkinsonism-dementia of Guam. Ann Neurol 25: 146-151

Spillantini M G, Bird T D, Ghetti B (1998) Frontotemporal dementia and Parkinsonism linked to chromosome 17: A new group of tauopathies. Brain Path 8: 387-402

Studier F W, Moffatt B A (1986) Use of bacteriophage T7 RNA polymerase to direct selective high-level expression of cloned genes. J Mol Biol 189:113-130

Thorpe S J, Kerr M A (1994) Common immunological techniques: ELISA, blotting, immunohistochemistry and immunocytochemistry. Immunochemistry BIOS Scientific publisher limited Oxford: 185-209

Vallee R B (1986) Reversible assembly punTication of microtubules without assembly-promoting agents and further purification of tubulin, microtubule-associated proteins, and MAP fragments. Methods Enzymol, 134: 89-104

Walls K, Azhar 5, Rho M, Lewis 5, Cowan N, Murphy D (1993) The mechanism of equilibrium binding of microtubule-associated protein 2 to microtubules. Binding is a multi-phasic process and exhibits positive coopeantivity. J Biol Chem 20: 15158-15167

Wang J -Z; Grundke-Iqbal I; Iqbal K (1996) Glycosylation of microtubule-associated protein tau: An abnormal post-translational modification in Alzheimer's disease. Nature Med 2; 871-875

Wilson D M, Binder L I (1997) Free fatty acids stimulate the polymerization of tau and amyloid b peptides. In vitro evidence for a common effector of pathogenesis in Alzheimer's disease. Am J Pathol 150: 2181-2195

Wischik C M, Novak M, Edwards P C, Klug A, Tichelaar W, Crowther R A (1988a) Structural characterization of the core of the paired helical filament of Alzheimer disease. Proc Natl Acad Sci USA 85: 4884-4888

Wischik C M, Novak M, Trogersen H C, Edwards P C, Runswick M J, Jake R, Walker J E, Milstein C, Roth M, Klug A (1988b) Isolation of a fragment of tau derived from the core of the paired helical filament of Alzheimer disease, Proc Natl Acad USA 85: 4506-4510

Yan S -D, Chen X, Schmid A -M, Brett J, Godman G, Zou Y -S, Scott C W, Caputo C, Frappier T, Smith M A, Perry G, Yen S H, Stem D (1994) Glycated tau protein in Alzheimer disease: A mechanism for induction of oxidant stress. Proc Natl Acad SC' USA 91: 7787-7791

---

The invention claimed is:

1. An isolated DC-11 or DC-11/I antibody as produced by hybridoma cell line DC-11 (ECACC Deposit No: 00082215) or DC-11/I (ECACC Deposit No: 00082216).

2. A hybridoma cell line DC-11 (ECACC Deposit No: 00082215) or DC-11/I (ECACC Deposit No: 00082216).

3. A kit for detecting or isolating truncated forms of human tau protein in a sample of brain tissue or body fluid comprising a DC-11 or DC-11/I antibody as produced by hybridoma cell line DC-11 (ECACC Deposit No: 00082215) or DC-11/I (ECACC Deposit No: 00082216).

4. The kit of claim 3, further defined as comprising means for detecting the binding event of said antibody binding to said truncated forms of human tau protein.

5. The kit of claim 4, wherein the means for detecting the binding event is further defined as a secondary antibody.

6. The kit of claim 5, wherein the secondary antibody is specifically labeled.

7. The kit of claim 3, further comprising a standard preparation of said truncated forms of human tau protein.

8. A method for detecting truncated forms of human tau protein comprising:
mixing a sample of brain tissue or cerebral spinal fluid with a DC-11 or DC-11/I antibody as produced by hybridoma cell line DC-11 (ECACC Deposit No: 00082215) or DC-11/I (ECACC Deposit No: 00082216); and
detecting the presence of a binding event between said antibody and said truncated form of human tau protein.

9. The method of claim 8, further comprising measuring an amount of said truncated form of human tau protein being bound to said antibody.

10. The method of claim 8, wherein detecting the binding event comprises using a secondary antibody.

11. The method of claim 10, wherein the secondary antibody is specifically labeled.

12. The method of claim 8, further defined as comprising quantifying the truncated forms of human tau protein.

13. The method of claim 12, wherein quantifying the truncated forms of human tau protein comprises using a standard preparation of said truncated forms of human tau protein as a control in the sample.

14. The method of claim 8, wherein detecting truncated forms of human tau protein indicates Alzheimer's disease pathology in the sample.

* * * * *

UNITED STATES PATENT AND TRADEMARK OFFICE
CERTIFICATE OF CORRECTION

| | |
|---|---|
| PATENT NO. | : 7,446,180 B2 |
| APPLICATION NO. | : 10/470928 |
| DATED | : November 4, 2008 |
| INVENTOR(S) | : Michal Novak |

It is certified that error appears in the above-identified patent and that said Letters Patent is hereby corrected as shown below:

In claim 5, column 39, line 61, delete "farther" and insert --further-- therefor.

Signed and Sealed this

Twenty-seventh Day of January, 2009

JOHN DOLL
*Acting Director of the United States Patent and Trademark Office*

UNITED STATES PATENT AND TRADEMARK OFFICE
CERTIFICATE OF CORRECTION

PATENT NO. : 7,446,180 B2
APPLICATION NO. : 10/470928
DATED : November 4, 2008
INVENTOR(S) : Michal Novak It is certified that error appears in the above-identified patent and that said Letters Patent is hereby corrected as shown below:

In title page, item (73) Assignee, delete "(AU)" and insert --AT-- therefor.

Signed and Sealed this

Second Day of June, 2009

JOHN DOLL
*Acting Director of the United States Patent and Trademark Office*